(12) United States Patent
Forsell

(10) Patent No.: US 9,351,840 B2
(45) Date of Patent: May 31, 2016

(54) HIP JOINT DEVICE, SYSTEM AND METHOD
(76) Inventor: Peter Forsell, Bouveret (CH)
(*) Notice: Subject to any disclaimer, the term of this patent is extended or adjusted under 35 U.S.C. 154(b) by 0 days.
(21) Appl. No.: 13/383,284
(22) PCT Filed: Jul. 12, 2010
(86) PCT No.: PCT/SE2010/050814
§ 371 (c)(1),
(2), (4) Date: Jan. 10, 2012
(87) PCT Pub. No.: WO2011/005195
PCT Pub. Date: Jan. 13, 2011
(65) Prior Publication Data
US 2012/0130504 A1 May 24, 2012

Related U.S. Application Data

(60) Provisional application No. 61/229,738, filed on Jul. 30, 2009, provisional application No. 61/229,739,
(Continued)

(30) Foreign Application Priority Data

| | | | |
|---|---|---|---|
| Jul. 10, 2009 | (SE) | ................................ | 0900957 |
| Jul. 10, 2009 | (SE) | ................................ | 0900958 |
| Jul. 10, 2009 | (SE) | ................................ | 0900959 |
| Jul. 10, 2009 | (SE) | ................................ | 0900960 |
| Jul. 10, 2009 | (SE) | ................................ | 0900962 |
| Jul. 10, 2009 | (SE) | ................................ | 0900963 |
| Jul. 10, 2009 | (SE) | ................................ | 0900965 |
| Jul. 10, 2009 | (SE) | ................................ | 0900966 |
| Jul. 10, 2009 | (SE) | ................................ | 0900968 |
| Jul. 10, 2009 | (SE) | ................................ | 0900969 |
| Jul. 10, 2009 | (SE) | ................................ | 0900970 |
| Jul. 10, 2009 | (SE) | ................................ | 0900972 |
| Jul. 10, 2009 | (SE) | ................................ | 0900973 |
| Jul. 10, 2009 | (SE) | ................................ | 0900974 |
| Jul. 10, 2009 | (SE) | ................................ | 0900976 |
| Jul. 10, 2009 | (SE) | ................................ | 0900978 |
| Jul. 10, 2009 | (SE) | ................................ | 0900981 |

(51) Int. Cl.
*A61F 2/36* (2006.01)
*A61B 17/16* (2006.01)
*A61F 2/30* (2006.01)
*A61F 2/46* (2006.01)

(52) U.S. Cl.
CPC ........... *A61F 2/3601* (2013.01); *A61B 17/1666* (2013.01); *A61F 2/30734* (2013.01);
(Continued)

(58) Field of Classification Search
CPC . A61F 2/36; A61F 2/3601; A61F 2002/2828; A61F 17/74
USPC ................. 623/23.11, 23.12, 23.14, 23.42
See application file for complete search history.

(56) References Cited

U.S. PATENT DOCUMENTS 5,800,553 A 9/1998 Albrektsson et al.
6,488,716 B1 * 12/2002 Huang et al. ............... 623/23.12
(Continued)

FOREIGN PATENT DOCUMENTS

WO WO 00/09038 2/2000

OTHER PUBLICATIONS

International Search Report for PCT/SE2010/050814, mailed Nov. 15, 2010.

*Primary Examiner* — David Isabella
*Assistant Examiner* — Christine Nelson

(57) ABSTRACT

A medical device for treating hip joint osteoarthritis in a human patient is provided, the hip joint comprises an acetabulum, being a part of the pelvic bone, and a caput femur, being connected to the collum femur and being the upper extremity of the femoral bone. The caput femur and collum femur further comprises cortical bone, the outer more sclerotic bone, and cancellous bone, placed in the bone marrow, said medical device comprising: an artificial caput femur surface, adapted to be in contact with the acetabulum surface or an artificial replacement therefor, and a fixating member adapted to at least partly be stabilized by the cortical bone of a stabilizing part of the collum femur.

18 Claims, 18 Drawing Sheets

Related U.S. Application Data filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(52) U.S. Cl.
CPC ............. *A61F2002/30729* (2013.01); *A61F 2002/4631* (2013.01); *A61F 2002/4649* (2013.01); *A61F 2310/00359* (2013.01)

(56) References Cited

U.S. PATENT DOCUMENTS

| 6,824,568 | B1 | 11/2004 | Albrektsson et al. | |
|---|---|---|---|---|
| 2003/0130741 | A1 | 7/2003 | McMinn | |
| 2004/0024468 | A1* | 2/2004 | Lualdi et al. | 623/22.45 |
| 2005/0010230 | A1 | 1/2005 | Crofford | |
| 2008/0154379 | A1* | 6/2008 | Steiner et al. | 623/17.16 |
| 2009/0076619 | A1 | 3/2009 | Grappiolo et al. | |
| 2010/0125341 | A1* | 5/2010 | Frauens | 623/23.6 |
| 2010/0168866 | A1* | 7/2010 | Shih | 623/23.14 |
| 2012/0116530 | A1* | 5/2012 | Forsell | 623/23.11 |
| 2012/0116534 | A1* | 5/2012 | Forsell | 623/23.14 |

\* cited by examiner

A - A

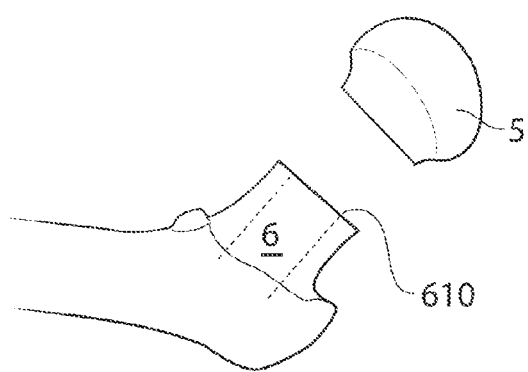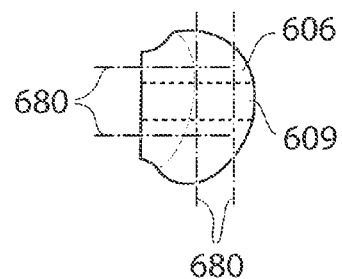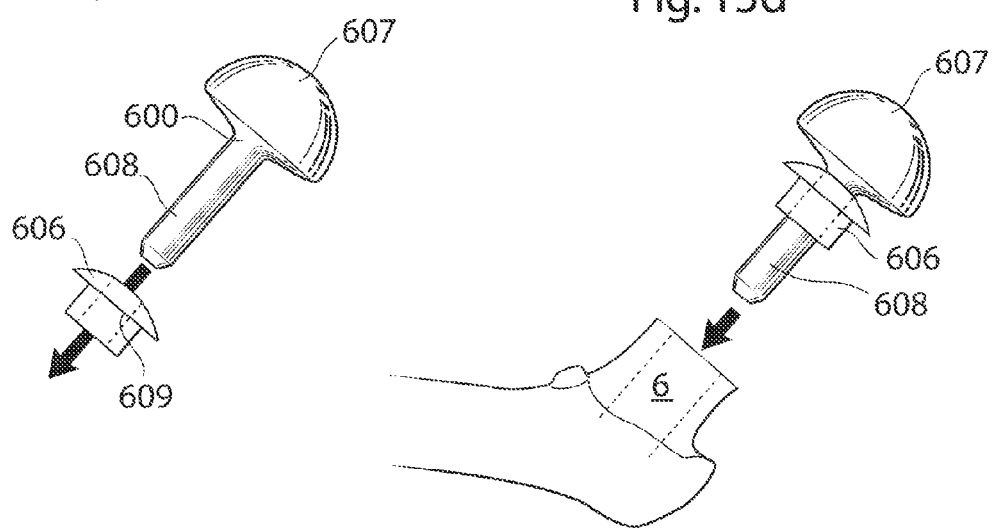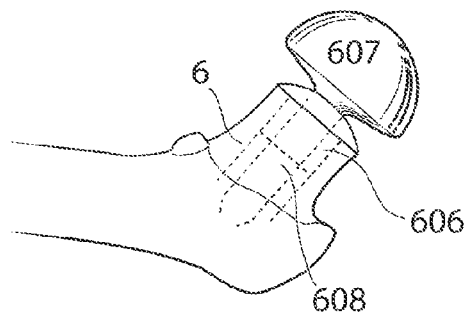

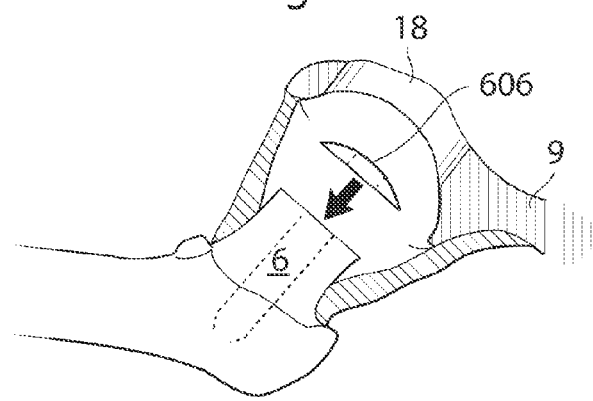
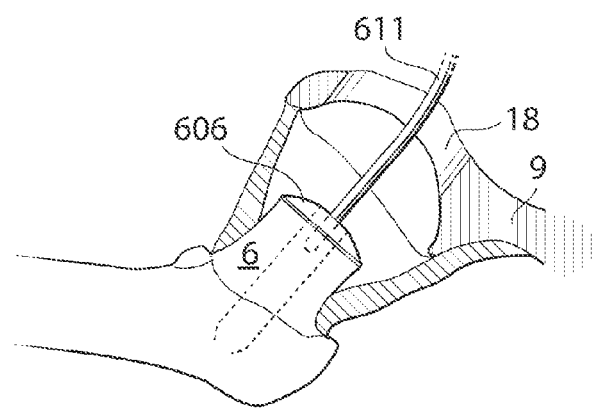
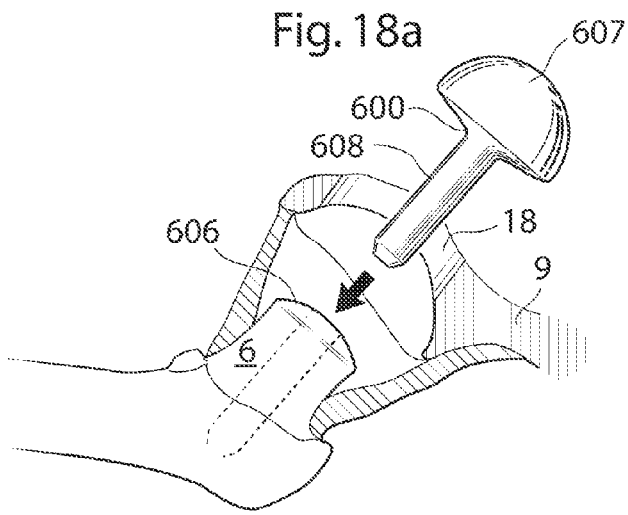
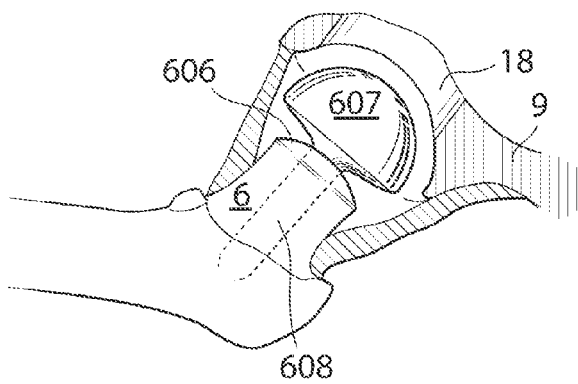

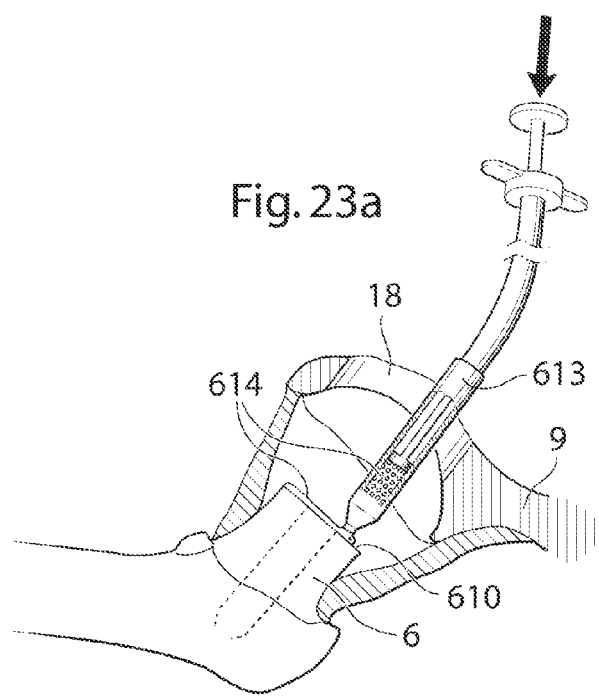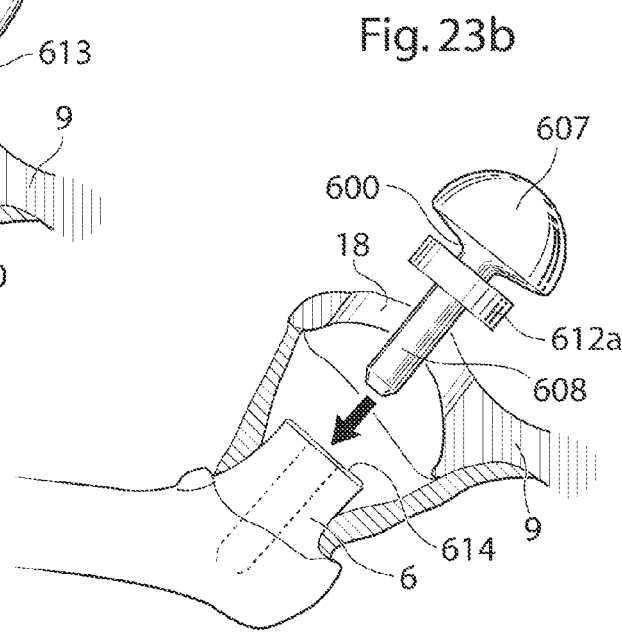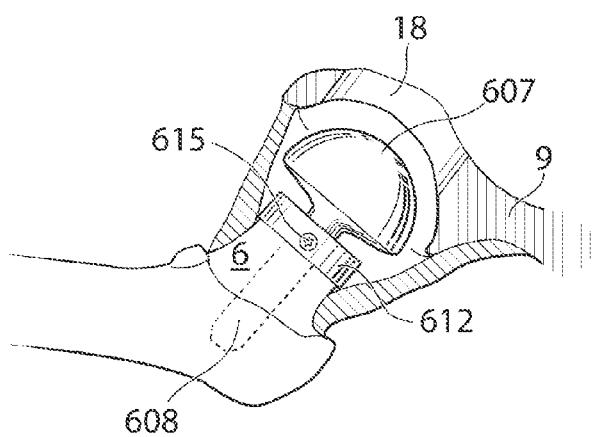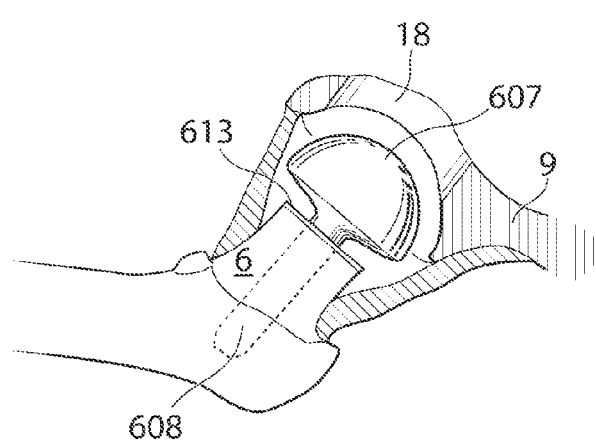

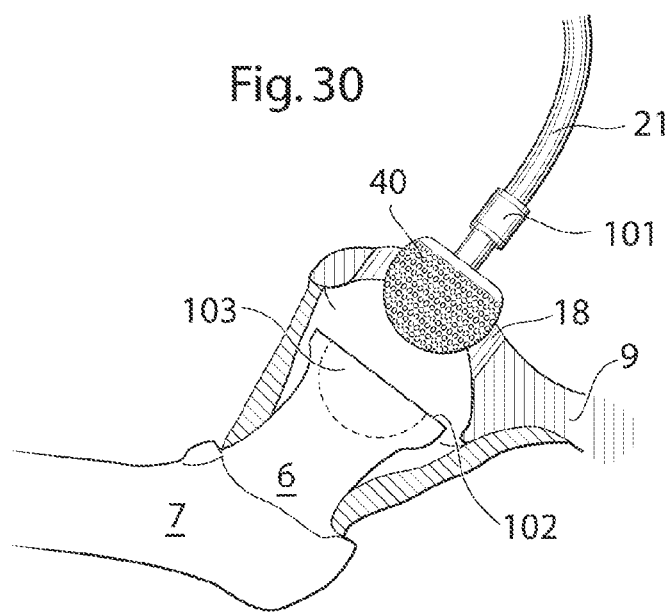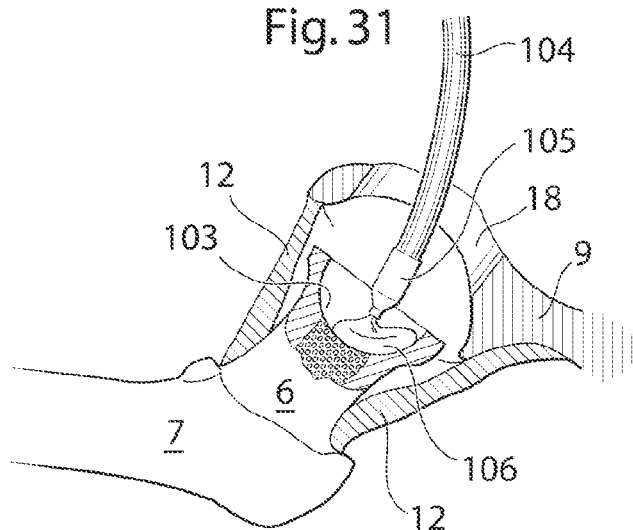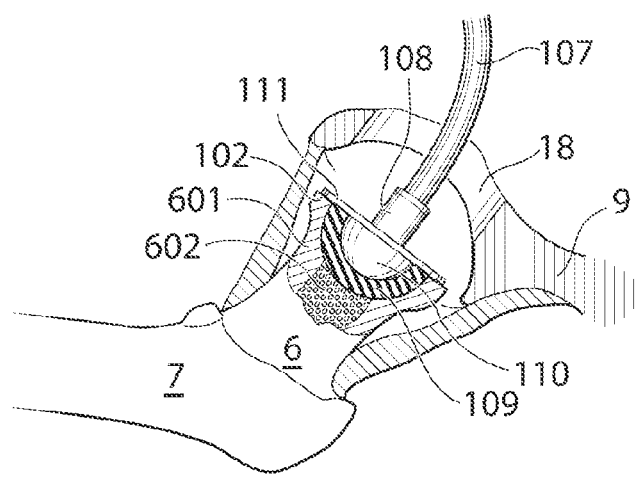

HIP JOINT DEVICE, SYSTEM AND METHOD

This application is the U.S. national phase of International Application No. PCT/SE2010/050814, filed 12 Jul. 2010, which designated the U.S. and claims the benefit of U.S. Provisional Nos. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device adapted to be fixated to the collum femur of a patient and a surgical or laparoscopic/arthroscopic method of fixating a medical device to the collum femur 6.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through a lateral incision in the hip and upper thigh and through, Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

SUMMARY

According to one embodiment, a medical device for treating hip joint osteoarthritis in a human patient is provided. The hip joint comprises an acetabulum, being a part of the pelvic bone, and a caput femur being connected to the collum femur and being the upper extremity of the femoral bone. The caput femur and collum femur further comprises cortical bone, the outer more sclerotic bone, and cancellous bone, placed in the bone marrow. The medical device comprises: An artificial caput femur surface, adapted to be in contact with the acetabulum surface or an artificial replacement therefor, and a fixating member adapted to at least partly be stabilized by the cortical bone of a stabilizing part of the collum femur.

According to one embodiment, the collum femur has a longitudinal extension and the fixating member is adapted to at least partly be stabilized by the cortical bone of the stabilizing part of the collum femur. The stabilizing is performed from the inside, substantially perpendicular to the longitudinal extension, and from the acetabulum side, substantially in line with the longitudinal extension.

According to one embodiment the collum femur has a longitudinal extension and the fixating member is adapted to at least partly be stabilized by the cortical bone of the stabilizing part of the collum femur. The stabilizing is performed from the inside, substantially perpendicular to the longitudinal extension, from the acetabulum side, substantially in line with the longitudinal extension, and from the outside, substantially perpendicular to the longitudinal extension.

According to one embodiment the collum femur has a longitudinal extension and the fixating member is adapted to at least partly be stabilized by the cortical bone of the stabilizing part of the collum femur. The stabilizing is performed from the inside, substantially perpendicular to the longitudinal extension, and from the outside, substantially perpendicular to the longitudinal extension.

According to one embodiment the collum femur has a longitudinal extension and the fixating member is adapted to at least partly be stabilized by the cortical bone of the stabilizing part of the collum femur. The stabilizing is performed from the acetabulum side, substantially in line with the longitudinal extension, and from the outside, substantially perpendicular to the longitudinal extension.

In any of the embodiments the fixating member could further be positioned on the collum femur.

The stabilizing part in any of the embodiments could be defined to be the proximal half of the collum femur, the proximal two third of the collum femur, the proximal three quarter of the collum femur, the proximal 90% of the collum femur or the whole collum femur.

According the one embodiment the fixating member is adapted to at least partly be directly stabilized by the cortical bone of the stabilizing part of the collum femur, however it is also conceivable that the fixating member is adapted to at least partly be indirectly stabilized by the cortical bone of the stabilizing part of the collum femur, in which case a material could be placed between the fixating member and the cortical bone of the stabilizing part of the collum femur. The material could be at least one of: bone cement, an at least partly elastic material, glue, adhesive, antibiotic, biocompatible plastic material, biocompatible ceramics or biocompatible metal.

According to one embodiment the medical device further comprises a stabilizing member, adapted to stabilize the fixating member. The stabilizing member interconnects the outer collum femur surface, at least on two opposite sides thereof. The stabilizing member could comprises a piece of bone, which could be a piece of bone removed from the caput femur of the human patient.

According to one embodiment the caput femur comprises a caput femur surface area, and the artificial caput femur surface comprises a caput femur surface area. The artificial caput femur surface area could be smaller than the caput femur surface area, hence the artificial caput femur is smaller than the caput femur of the human patient.

According to one embodiment the fixating member further comprises a mechanical connection adapted to mechanically connect to the cortical bone of the stabilizing part of the collum femur, on the inside and/or the outside thereof. It is further conceivable that the mechanical connection is adapted to indirectly connect to the cortical bone of the stabilizing part of the collum femur on the inside and/or the outside thereof.

The fixating according to any of the embodiments could comprise at least one of: at least one screw, form fitting, welding, adhesive, at least one sprint, at least one band, and other mechanical connecting members.

According to one embodiment the medical device comprises at least two parts. The at least two parts are adapted to be mechanically connected after insertion in the hip joint. The mechanical connection could be achieved using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

A medical device for treating hip joint osteoarthritis in a human patient is further provided. The hip joint comprises an acetabulum being a part of the pelvic bone, and a caput femur being connected to the collum femur and being the upper extremity of the femoral bone. The caput femur and collum femur further comprises cortical bone, the outer more sclerotic bone, and cancellous bone, placed in the bone marrow. The medical device comprises: an artificial caput femur surface adapted to be in contact with the acetabulum surface or an artificial replacement therefor, and a fixating member adapted to at least partly be stabilized by the cortical bone of a stabilizing part of the collum femur. The fixating member comprises a stabilizing member comprising a piece of natural cortical bone adapted to be connected to the cortical bone of the collum femur.

According to one embodiment, the piece of bone comprises a piece of bone from the caput femur.

According to another embodiment, at least a portion of the piece of bone is adapted to be placed on the inside of the collum femur for stabilizing the medical device from the inside of the collum femur.

According to another embodiment, at least a portion of the piece of bone is adapted to be placed on a cut side of the collum femur facing the acetabulum for stabilizing the medical device from the acetabulum side of the collum femur.

According to another embodiment, at least a portion of the piece of bone is adapted to be placed on the outside of the collum femur for stabilizing the medical device from the outside of the collum femur.

According to another embodiment, the piece of bone comprises a cavity adapted to receive the collum femur or surgically modified collum femur.

According to another embodiment, the medical device comprises an elongated fixating member adapted to be inserted into the collum femur, and wherein the elongated member extends through the piece of bone.

According to another embodiment, the medical device further comprises a fixating member adapted to at least partly be stabilized by the cortical bone of a stabilizing part of the collum femur, from the inside of the collum femur, substantially perpendicular to the longitudinal extension, and from the acetabulum side of the collum femur, substantially in line with the longitudinal extension.

According to another embodiment, the medical device further comprises a fixating member, and wherein said fixating member is adapted to at least partly be stabilized by the cortical bone of a stabilizing part of the collum femur from the inside of the collum femur, substantially perpendicular to the longitudinal extension, from the acetabulum side of the collum femur, substantially in line with the longitudinal extension, and from the outside of the collum femur, substantially perpendicular to the longitudinal extension.

According to another embodiment, the medical device further comprises a fixating member adapted to at least partly be stabilized by the cortical bone of a stabilizing part of the collum femur from the inside of the collum femur, substantially perpendicular to the longitudinal extension, and from the outside of the collum femur, substantially perpendicular to the longitudinal extension.

According to another embodiment the medical device further comprises a fixating member. The fixating member is adapted to at least partly be stabilized by the cortical bone of a stabilizing part of the collum femur from the acetabulum side of the collum femur, substantially in line with the longitudinal extension, and from the outside of the collum femur, substantially perpendicular to the longitudinal extension.

According to another embodiment the medical device further comprises a stabilizing member adapted to stabilize the medical device on the outside of the collum femur, wherein the stabilizing member is adapted to at least partially cover the piece of bone on the acetabulum side of the piece of bone.

Introduction

According to one embodiment medical device is adapted to be introduced into the hip joint through a hole in at least one of the pelvic bone, the femoral bone and/or the hip joint capsule.

The medical device could further comprise an attaching member adapted to attach the medical device to a surgical instrument adapted to insert the medical device into the hip joint through a hole.

Material

The medical device could comprise at least one of the materials: stainless steel, titanium or titanium alloys, fluoropolymers and/or an elastic material. It is furthermore conceivable that the medical device comprises a first material adapted to be elastic and a second material adapted to be less elastic than said first material.

According to one embodiment the surface of the medical device is porous which for one thing facilitates the fixation of the medical device to bone.

System

A medical device system for treating hip joint osteoarthritis in a human patient is further provided. The hip joint comprises an acetabulum, being a part of the pelvic bone, and a caput femur, being connected to the collum femur and being the upper extremity of the femoral bone. The collum femur and caput femur further comprises cortical bone and cancellous bone. The medical device system comprises a medical device, comprising an artificial caput femur surface adapted to be in contact with the acetabulum surface or an artificial replacement therefor, and a fixating member adapted to at least partly be positioned on the inside of the cortical bone of the collum femur. The fixating member is adapted to use a part of the cortical bone of the caput femur, removed from the caput femur, to assist the fixating member in the fixation of the medical device.

According to one embodiment the part of the cortical bone of the caput femur, removed from the caput femur, is mechanically fixated to the medical device. It is furthermore conceivable that the cortical bone of the caput femur, removed from the caput femur, is adapted to be placed in connection with the cortical bone of the collum femur.

The hip joint comprises a ball shaped caput femur, as the proximal part of the femoral bone with a convex hip joint surface and a cup shaped acetabulum as part of the pelvic bone with a concave hip joint surface. According to one embodiment the medical device comprises an artificial convex hip joint surface, adapted to be fixated to the pelvic bone, and an artificial concave hip joint surface, adapted to be fixated to the collum femur.

Introduction

According to one embodiment medical device system is adapted to be introduced into the hip joint through a hole in at least one of the pelvic bone, the femoral bone and/or the hip joint capsule.

The medical device system could further comprise an attaching member, adapted to attach the medical device to a surgical instrument adapted to insert the medical device into the hip joint through a hole.

Second System

A medical device system for treating hip joint osteoarthritis in a human patient is further provided. The hip joint comprises an acetabulum being a part of the pelvic bone, and a caput femur being connected to the collum femur and being the upper extremity of the femoral bone. The collum femur and caput femur further comprises cortical bone and cancellous bone. The system comprises the medical device according to any of the embodiments above, and an artificial acetabulum surface.

According to one embodiment the artificial acetabulum surface is adapted to be in connection with the pelvic bone, and carry the load placed on the artificial acetabulum surface from the weight of the human patient by the contact with the medical device.

According to one embodiment the artificial acetabulum surface comprises at least one supporting member, which in turn could comprise at least one of: at least one screw, adhesive, at least one plate, bone cement, a section of said artificial acetabulum, and any other mechanical supporting construction.

According to one embodiment the artificial acetabulum surface comprises a first and second part, the second part could be adapted to: be displaceable in relation to said first part, carry the load by the connection with the pelvic bone, and carries said load when displaced.

According to one embodiment the artificial acetabulum surface comprises at least two artificial acetabulum surface parts. The at least two artificial acetabulum surface parts could be adapted to be connected or attached to each other after insertion in a hip joint of a human patient. The at least two artificial acetabulum surface parts could further be adapted to be mechanically connected using: at least one screw, adhesive, at least one plate, bone cement, a section of said artificial acetabulum, and any other mechanical supporting construction.

According to one embodiment the artificial acetabulum surface is adapted to have a varying size for insertion through a hole in the pelvic bone from the opposite side from acetabulum. The varying size is adapted to vary, at the time of insertion through the hole, between being both smaller and larger than the hole in the pelvic bone, thus allowing or not allowing the artificial acetabulum surface to pass through the hole.

According to one embodiment the medical device system, further comprises a mold, or parts for sealing a space, adapted to be used in the creation of the artificial acetabulum surface.

Method

A surgical method of treating a hip joint of a human patient by providing a medical device is further provided. The hip joint comprises an acetabulum, being a part of the pelvic bone, and a caput femur, being connected to the proximal part of the collum femur and being the upper extremity of the femoral bone. The collum femur and caput femur further comprises cortical bone and cancellous bone. The surgical method comprises the steps of cutting the skin of the human patient, dissecting an area of the pelvic bone on the opposite side from the acetabulum, creating a hole in the dissected area, the hole passing through the pelvic bone and into the hip joint of the human patient. Furthermore the method comprises the steps of removing, at least partly, the caput femur from the femoral bone, removing a part of the cortical bone of the caput femur from the caput femur, attaching the part of the cortical bone of the caput femur to a medical device, and attaching the medical device with the part of the cortical bone of the caput femur to the collum femur.

A laparoscopic/arthroscopic method of treating a hip joint of a human patient by providing a medical device is further provided. The hip joint comprises an acetabulum, being a part of the pelvic bone, and a caput femur, being connected to the proximal part of the collum femur and being the upper extremity of the femoral bone. The collum femur and caput femur further comprises cortical bone and cancellous bone, the laparoscopic/arthroscopic method comprises the steps of: inserting a needle or a tube like instrument into the patient's body, using the needle or tube like instrument to fill a part of the patient's body with gas and thereby expanding a cavity within said body, placing at least two laparoscopic/arthroscopic trocars in said cavity, inserting a camera through one of the laparoscopic/arthroscopic trocars into the cavity, inserting at least one dissecting tool through one of the at least two laparoscopic/arthroscopic trocars, dissecting an area of the pelvic bone on the opposite side from the acetabulum, creating a hole in the dissected area passing through the pelvic bone and into the hip joint of the human patient, removing, at least partly, the caput femur from the femoral bone, removing a part of the cortical bone of the caput femur from the caput femur, attaching said part of said cortical bone of the caput femur to a medical device, and attaching the medical device with the part of the cortical bone of the caput femur to a stabilizing part of the collum femur.

A surgical method of treating a hip joint of a human patient, by providing a medical device according to any of the embodiments above is further provided. The hip joint comprises an acetabulum, being a part of the pelvic bone, and a caput femur being connected to the proximal part of the collum femur and being the upper extremity of the femoral bone. The collum femur and caput femur further comprises cortical bone, outer sclerotic bone, and cancellous bone, in the bone marrow, the surgical method comprises the steps of: cutting the skin of the human patient, dissecting an area of the hip, removing, at least partly, the caput femur from the femoral bone, sparing the proximal part of the collum femur, attaching the fixating member to the proximal part of the collum femur, direct or indirect, and placing the artificial caput femur surface in the acetabulum or an artificial acetabulum replacement, and closing the wounds, if necessary in steps.

According to one embodiment the collum femur has a longitudinal extension and the fixating member is at least partly positioned on and stabilized by the cortical bone of the stabilizing part of the collum femur from two different aspects of the collum femur. The method further comprises the steps of: positioning and stabilizing said fixating member from the inside of the stabilizing part of the collum femur, substantially perpendicular to the longitudinal extension thereof, and from the acetabulum side substantially in line with the longitudinal extension of the collum femur.

According to one embodiment the collum femur has a longitudinal extension and the fixating member is at least partly positioned on and stabilized by the cortical bone of the stabilizing part of the collum femur from three different aspects of the collum femur. The method further comprises the steps of: positioning and stabilizing the fixating member from the inside of the stabilizing part of the collum femur substantially perpendicular to the longitudinal extension thereof, from the acetabulum side substantially in line with the longitudinal extension of the collum femur and from the outside of the collum femur substantially perpendicular to the longitudinal extension thereof.

According to one embodiment the collum femur has a longitudinal extension and the fixating member is at least partly positioned on and stabilized by the cortical bone of the stabilizing part of the collum femur from two different aspects of the collum femur. The method further comprises the steps of: positioning and stabilizing the fixating member from the inside of the stabilizing part of the collum femur substantially perpendicular to the longitudinal extension thereof and from the outside of the stabilizing part of the collum femur substantially perpendicular to the longitudinal extension thereof.

According to one embodiment the collum femur has a longitudinal extension and the fixating member is at least partly positioned on and stabilized by the cortical bone of the stabilizing part of the collum femur from two different aspects of the collum femur. The method further comprises the steps of: positioning and stabilizing the fixating member from the acetabulum side substantially in line with the longitudinal extension of the collum femur and from the outside of the stabilizing part of the collum femur substantially perpendicular to the longitudinal extension thereof.

The stabilizing part of collum femur could be defined to be the proximal half of the collum femur, the proximal two thirds of the collum femur, the proximal three quarter of the collum femur, the proximal 90% of the collum femurm or the whole collum femur.

The method according to claim 55, further comprising the step of placing a material between the fixating member and the cortical bone of said stabilizing part of the collum femur, said material being a material selected from a group consisting of; bone cement, any type of at least partly elastic material, glue, adhesive, antibiotic, biocompatible plastic material, biocompatible ceramics and biocompatible metal.

According the one embodiment the fixating member is adapted to at least partly be directly stabilized by the cortical bone of the stabilizing part of the collum femur, however it is also conceivable that the fixating member is adapted to at least partly be indirectly stabilized by the cortical bone of the stabilizing part of the collum femur, in which case a material could be placed between the fixating member and the cortical bone of the stabilizing part of the collum femur. The material could be at least one of: bone cement, an at least partly elastic material, glue, adhesive, antibiotic, biocompatible plastic material, biocompatible ceramics or biocompatible metal.

According to one embodiment the method further comprises the steps of: providing a stabilizing member, adapted to stabilize said fixating member, and interconnecting the outer collum femur surface, at least on two opposite sides thereof, perpendicular to the longitudinal extension of the collum femur.

According to one embodiment the stabilizing member further comprises a piece of bone.

According to one embodiment the method further comprises the steps of: extracting a piece of bone from the patient's caput femur, and placing said piece of bone onto the collum femur.

According to one embodiment the method further comprises the step of providing an artificial acetabulum surface, which in turn could be adapted to be in connection with the pelvic bone, and carry the load placed on the artificial acetabulum surface from the weight of the human patient by the contact with the medical device.

A laparoscopic/arthroscopic method of treating a hip joint of a human patient by providing the medical device according to any of the embodiment above is further provided. The hip joint comprises an acetabulum being a part of the pelvic bone, and a caput femur being connected to the collum femur and being the upper extremity of the femoral bone. The collum femur and caput femur further comprises cortical bone, outer sclerotic bone, and cancellous bone, in the bone marrow. The laparoscopic/arthroscopic method comprises the steps of: inserting a needle or a tube like instrument into the patient's body, using the needle or tube like instrument to fill a part of the patient's body with gas and thereby expanding a cavity within the body, placing at least two laparoscopic/arthroscopic trocars in the cavity, inserting a camera through one of the laparoscopic/arthroscopic trocars into the cavity, inserting at least one dissecting tool through one of the at least two laparoscopic/arthroscopic trocars, dissecting an area of the hip, removing, at least partly, the caput femur from the femoral bone, sparing a proximal part of the collum femur, attaching the fixating member to the proximal part of the collum femur, placing the artificial caput femur surface in the acetabulum or an artificial acetabulum replacement, and suturing in steps.

According to one embodiment the laparoscopic/arthroscopic method further comprises the step of removing a part of said cortical bone of the caput femur from the caput femur. The part of the cortical bone of the caput femur, removed from the caput femur, could be mechanically fixated to the medical device and/or be placed in connection with the cortical bone of the collum femur.

The laparoscopic/arthroscopic method could further comprise the step of providing an artificial acetabulum surface, which in turn could be adapted to be in connection with the pelvic bone, and carry the load placed on the artificial acetabulum surface from the weight of the human patient by the contact with the medical device.

According to one embodiment, the fixating member is operable to adjust the tightness of the stabilizing fixation to the collum femur.

According to one embodiment, the fixating member is operable to adjust the shape of the fixating member to better fit to the stabilizing fixation of the collum femur. The fixating member cold be operable by an adjustment device, the adjustment device could be operable by manual manipulation, or by a motor.

According to one embodiment, the collum and caput femur have a longitudinal collum caput center axis following the center of collum femur, wherein the fixating member is operable to adjust the shape of the fixating member for getting a distal closest part of the fixating member closer to the collum caput center axis than a more proximal closest part to the same center axis, thereby improving the stabilizing fixation to the femoral bone.

According to one embodiment, the stabilizing member is operable to adjust the tightness of the stabilizing fixation to the collum femur. The stabilizing member could be operable to adjust the shape of the fixating member to better fit to the stabilizing fixation of the collum femur. The stabilizing member could be operable by an adjustment device which could be operable by manual manipulation or by a motor.

According to one embodiment, the collum and caput femur has a longitudinal collum caput center axis following the center of collum femur. The fixating member could be operable to adjust the shape of the fixating member for getting a distal closest part of the fixating member closer to the collum caput center axis than a more proximal closest part to the same center axis, thereby improving the stabilizing fixation to the femoral bone.

Please note that any embodiment or part of embodiment as well as any method or part of method could be combined in any way.

BRIEF DESCRIPTION OF THE DRAWINGS

The invention is now described, by way of example, with reference to the accompanying drawings, in which:

FIGS. 15a and 15b shows the removing of a part of a piece of bone from the caput femur, FIG. 15c-15e shows the fixation of a medical device using a piece of bone, FIG. 17a shows the medical device with the piece of bone being inserted through a hole in the pelvic bone, FIG. 17b shows a surgical instrument adapted to fixate the piece of bone to the collum femur, FIG. 18a shows the medical device according to one embodiment, when it is being inserted through a hole in the pelvic bone, FIG. 18b shows the hip joint in section when the medical device has been provided, FIG. 23a shows a surgical instrument for applying adhesive to the surface of the section of the collum femur, FIG. 23b shows the medical device according to one embodiment being provided through the hole in the pelvic bone, FIG. 24a shows the hip joint in section when the medical device is fixated to the collum femur, FIG. 24b shows the hip joint in section when the medical device according to another embodiment, when fixated to the collum femur, FIG. 30 shows the step of reaming the collum femur from a hole in the pelvic bone, FIG. 31 shows the step of applying an adhesive to an area of the collum femur, FIG. 32 shows the step of placing an artificial hip joint surface in the collum femur.

DETAILED DESCRIPTION

Figure 1:
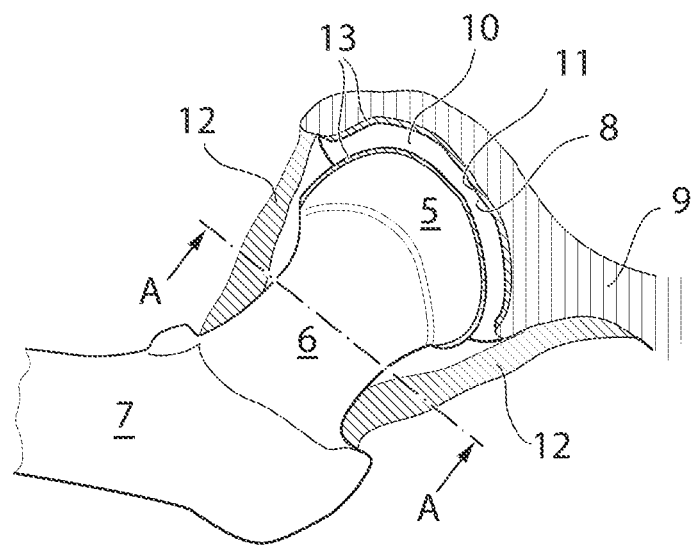
FIG. 1 a shows the hip joint in section.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements. The final position is to be understood as a functional position in which the medical device needs no further position change.

Arthroscopy is to be understood as key hole surgery performed in a joint, since the arthroscopic procedure could be performed in the abdomen of the patient some of the steps of this arthroscopic procedure is more laparoscopic/arthroscopic, however for the purpose of this invention the two terms arthroscopy and laparoscopy is used synonymously and for the purpose of this invention the main purpose of these methods are is that they are minimally invasive.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12, the patient can fully recover and place equal amount of strain on an artificial joint as is possible on a natural one.

Figure 1B:
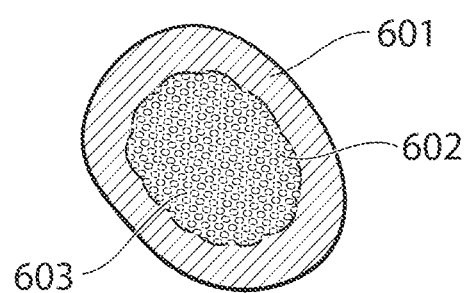
FIG. 1b shows the collum femur in section.

FIG. 1b shows the collum femur 6 in section. Both caput femur 5 and collum femur 6 further comprises cortical bone 601, the outer more sclerotic bone, and cancellous bone 602, placed in the bone marrow 603. The cortical bone is much more dense and beneficial to anchor a prosthesis two, whereas the cancellous bone 602 provides stability in the bone due to its sandwich construction, but is easy to remove to make room for a fixation member of a prosthesis.

Figure 2:
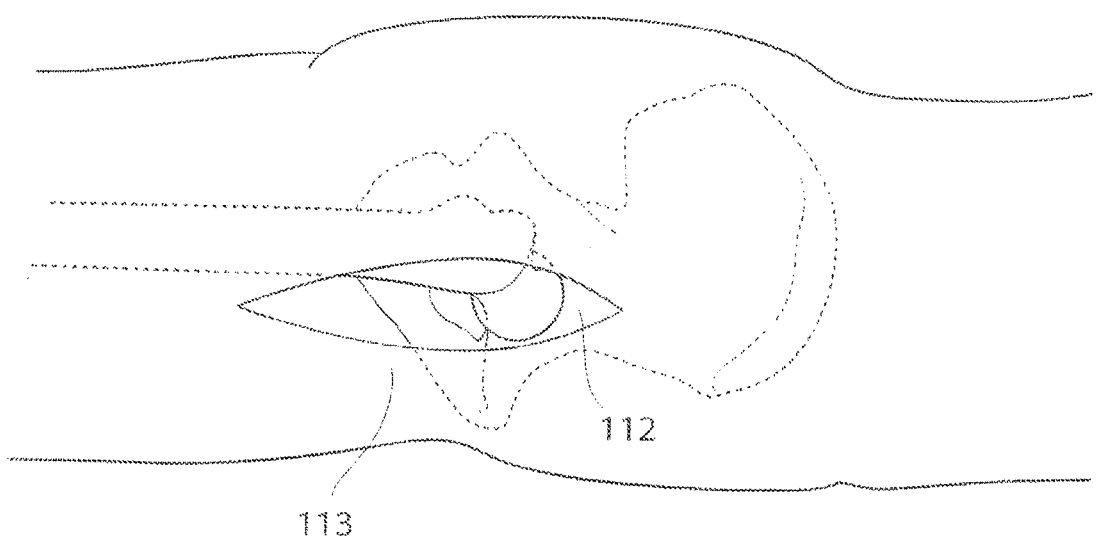
FIG. 2 shows a lateral view of the human patient in section when a conventional hip joint surgery is performed.

FIG. 2 shows a lateral view of a conventional hip joint surgery where an incision 112 is made in the thigh 113 enabling the surgeon to reach the femur bone 7 on which the caput femur 5 is located. In a conventional hip joint surgery the hip joint is accessed through the hip joint capsule, which forces the surgeon to, at least partly, savage the structure of said capsule.

Figure 3:
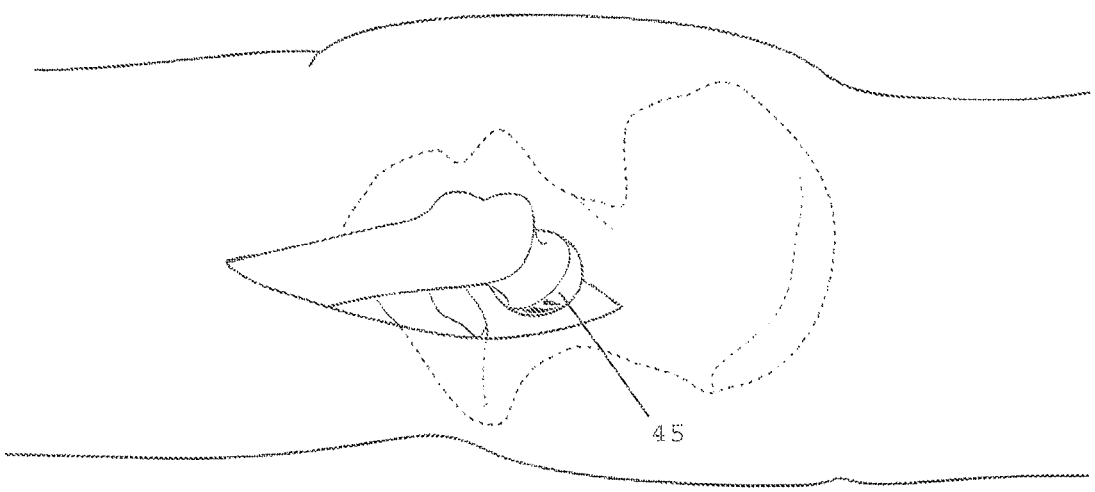
FIG. 3 shows a lateral view of the human patient when an artificial caput femur surface is provided to the femoral bone.

FIG. 3 shows the placing of an artificial caput femur surface 45 on the caput femur 5 in conventional surgery.

Figure 4:
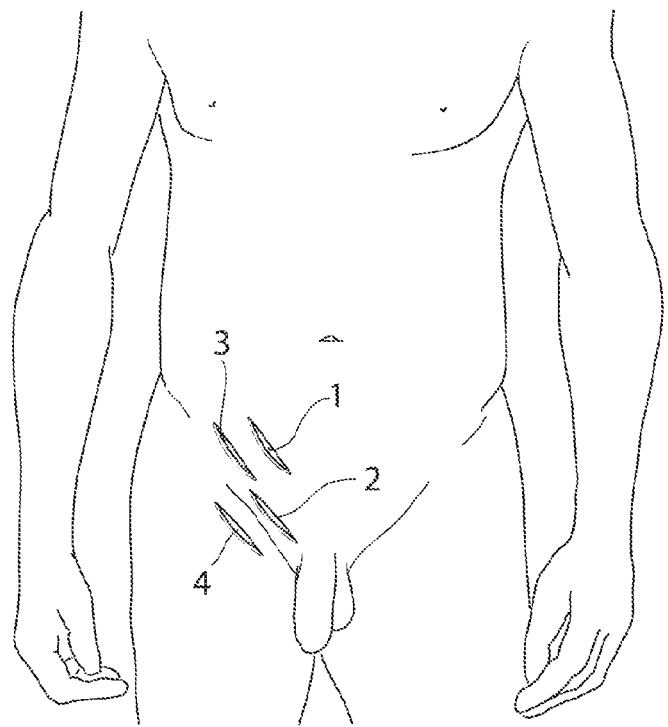
FIG. 4 shows a frontal view of the human patent when incisions have been made in a surgical method.

FIG. 4 shows a frontal view of the body of a human patient. A surgical method of operating the hip joint from the opposite side from acetabulum, is according to a first embodiment performed starting with an incision 1 in the abdominal wall of the human patient. The incision 1 passes through the rectus abdominis and peritoneum in to the abdomen of the human patient. In a second embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 5:
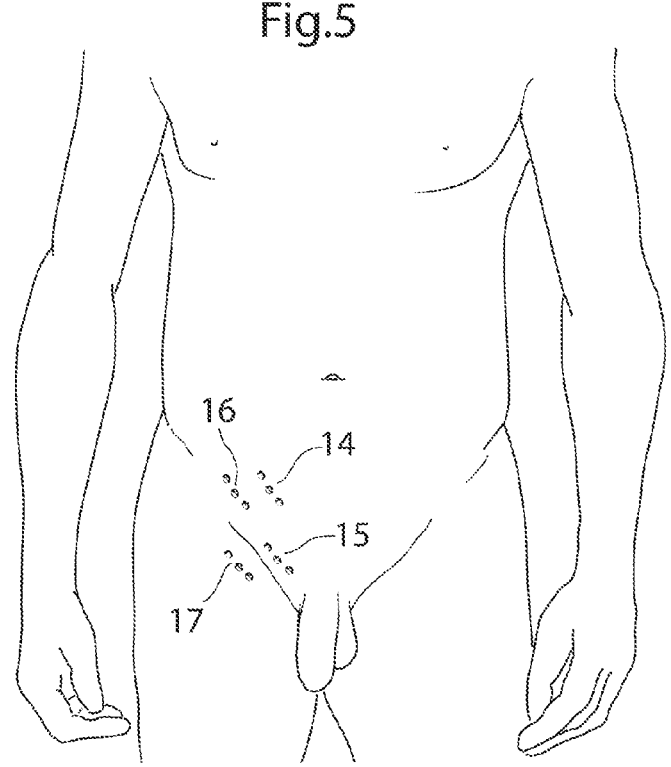
FIG. 5 shows a frontal view of the human patient when small incisions have been made in a laparoscopic/arthroscopic method.

FIG. 5 shows a frontal view of the body of a human patient. A laparoscopic/arthroscopic method of operating the hip joint, from the opposite side from acetabulum, is according to a first embodiment performed starting with making small incisions 14 in the abdominal wall of the human patient. The small incisions enable the surgeon to insert laparoscopic/arthroscopic trocars into the abdomen of the human patient. According to the first embodiment the incisions 14 passes through the abdominal wall, preferably rectus abdominis and peritoneum in to the abdomen of the human patient. According to a second embodiment the small incisions 15 is conducted through the abdominal wall, preferably rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

After the incision is made the surgical instruments according to any on the embodiments below can enter the human buoy and be used to assist the surgeon in the operation of the hip joint osteoarthritis.

Figure 6:
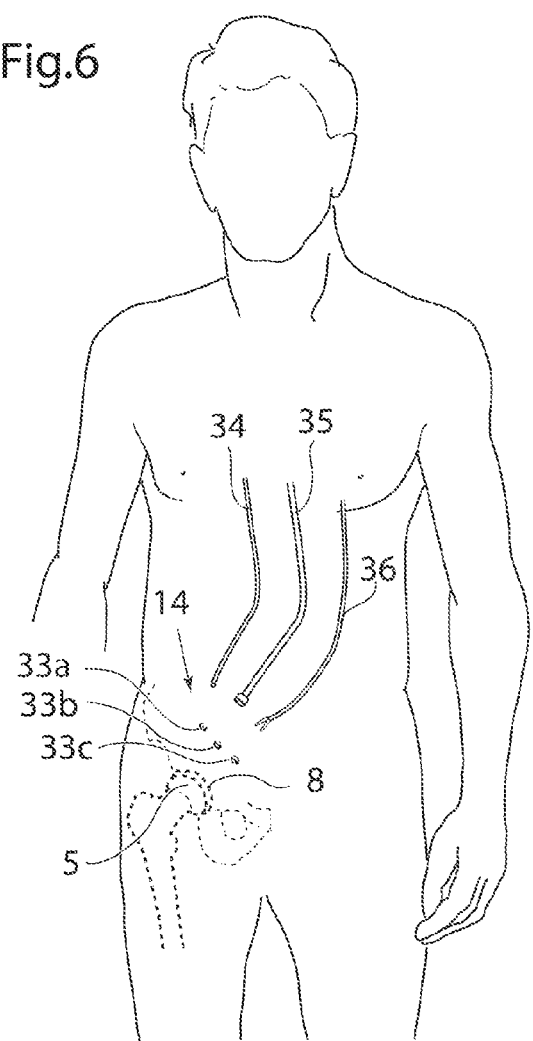
FIG. 6 shows a frontal view of a human patient when a laparoscopic/arthroscopic method is performed.

FIG. 6 shows a frontal view of the body of a human patient, illustrating the instruments 34, 35, 36 assisting in the method of operating the hip joint from the opposite side from acetabulum 8. The hip joint comprises the acetabulum 8 and the caput femur 5. The small incisions 14 in the abdominal wall of the human patient allows the insertion of laparoscopic/arthroscopic trocars 33a,b,c into the body of the patient. Whereafter one or more camera 34, a surgical instrument adapted to create a hole in the pelvic bone 35, or instruments 36 for introducing, placing, connecting, attaching, creating or filling prosthesis or prosthetic parts, can be inserted into said body through said laparoscopic/arthroscopic trocars 33a,b,c.

Figure 7:
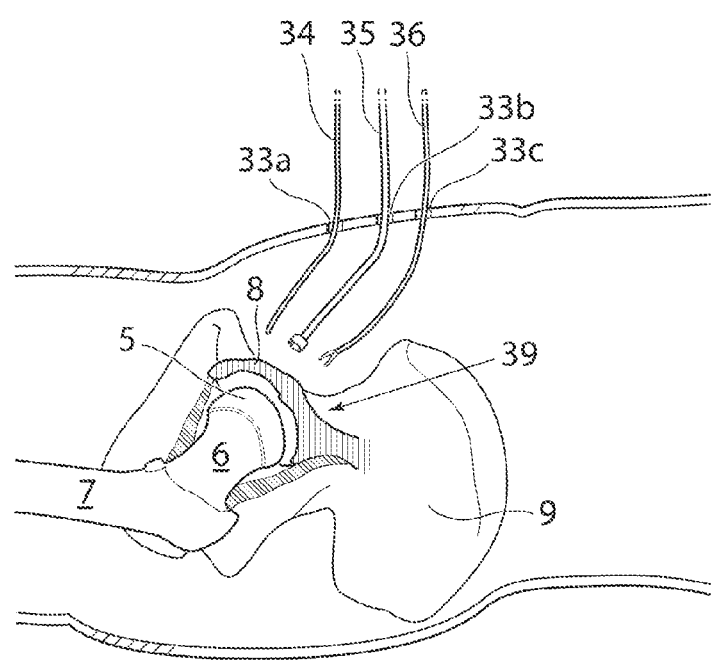
FIG. 7 shows the human patient in section when a laparoscopic/arthroscopic method is performed.

FIG. 7 shows a lateral view of the body of a human patient, with the hip joint shown in section in further detail. The hip joint comprises a caput femur 5 placed at the very top of collum femur 6 which is the top part of the femur bone 7. The caput femur is in connection with the acetabulum 8 which is a bowl shaped part of the pelvic bone 9. Laparoscopic/arthroscopic trocars 33a,b,c is being used to reach the hip joint 39 with one or more camera 34, a surgical instrument 35 adapted to create a hole in the pelvic bone 9, or instruments 36 for introducing, placing, connecting, attaching, creating or filling prosthesis or prosthetic parts.

After the instrument have been placed in the laparoscopic/arthroscopic trocars an area of the pelvic bone 9, on the opposite side from the acetabulum 8, is dissected, a needle or a tube like instrument is inserted into the patient's body, the needle or tube like instrument is used to fill a part of the patient's body with gas and thereby expanding a cavity within said body for allowing the surgeon to get a view through the at least one camera 34.

Figure 8:
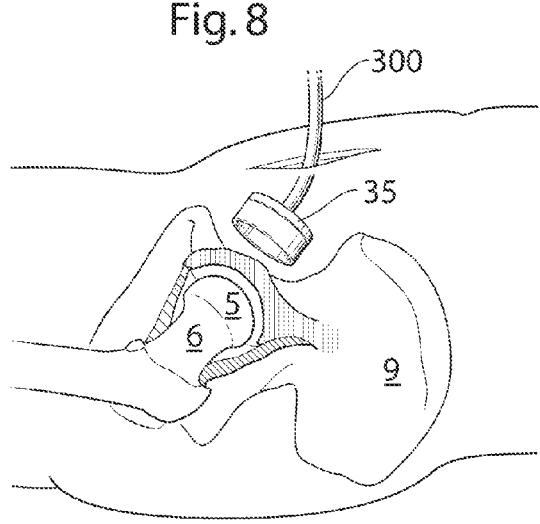
FIG. 8 shows the human patient in section when a medical device adapted to create a hole in the pelvic bone is provided.

FIG. 8 shows a lateral view of a human patient where a surgical instrument 35 adapted to create a hole in the pelvic bone from the abdominal side of the pelvic bone 9 is inserted through an incision in the abdominal wall. The surgical instrument could comprises a flexible part or section 300, enabling the surgical instrument to be very precisely adjusted to reach the pelvic bone or the hip joint from the abdominal side of the pelvic bone. The stiffness of said flexible part or section 300 could range from completely flexible to completely stiff to fit the surroundings of the particular operation. The surgical instrument 35 could be powered through an operating device which in turn could comprise an electrical, hydraulic, mechanical, pneumatic or magnetic engine and it could be adapted to create a rotating, oscillating, vibrating or repetitive movement.

According to another embodiment (not shown) the surgical instrument 35 is powered from an operating device being placed outside of the human body, in the thigh region. The force created in the operating device is then transferred through a force transferring member placed which is placed in the collum femur and femoral bone. This allows the surgeon to supply force to an area of the hip joint and its surroundings through an incision in the thigh.

Figure 9:
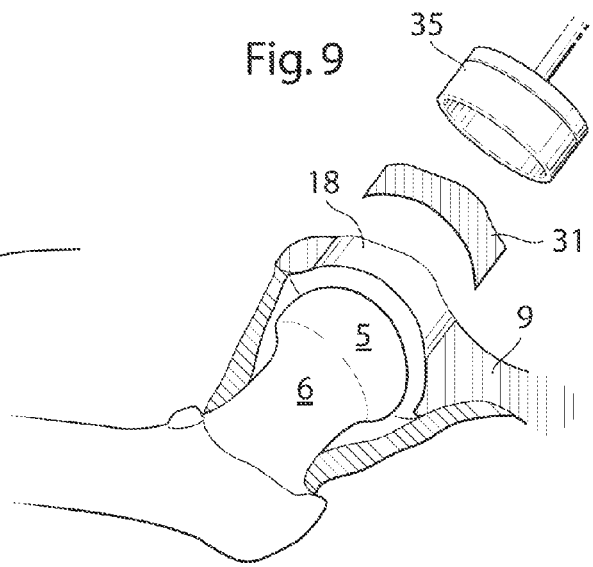
FIG. 9 shows the hip joint in section when a hole is being created in the pelvic bone.

FIG. 9 shows a hip joint in section wherein a surgical instrument 35 adapted to create a hole 18 in the pelvic bone 9 is adapted to create a bone plug 31. The bone plug 31 could be adapted to be replaced into said hole 18 after the surgical or laparoscopic/arthroscopic steps performed in the hip joint has been concluded.

Figure 10:
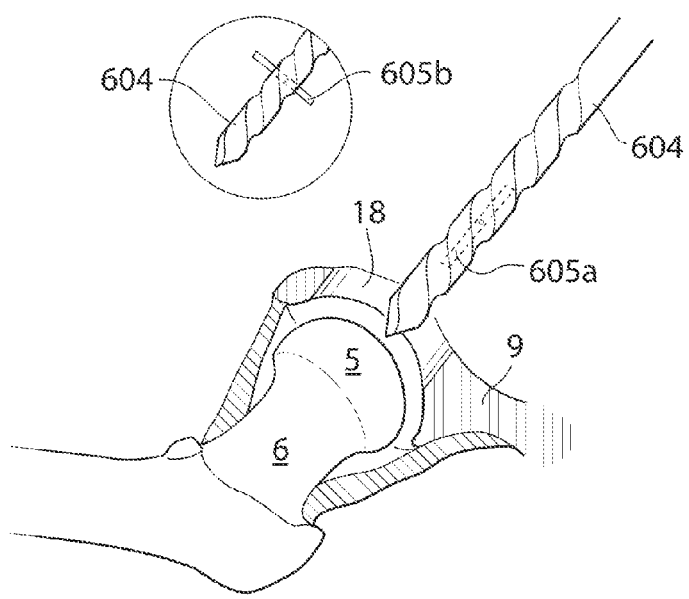
FIG. 10 shows the hip joint in section when a surgical instrument for removing the caput femur is provided.

FIG. 10 shows a hip joint in section wherein a surgical instrument 604 for removing the caput femur 5 is provided through a hole 18 in the pelvic bone 9. The surgical instrument is adapted to create a hole in the caput femur 5, passing down a longitudinal extension of the collum femur 6. The surgical instrument further comprises a sawing member 605a,b adapted to separate the caput femur from the collum femur. In a first state 605a, the sawing member 605a is retracted within the surgical instrument 604. When the surgical instrument is positioned inside of the collum femur in a desired position the sawing member is folded to a second state 605b allowing the sawing member to create a section in the collum femur, separating the caput femur 5 from the collum femur 6.

Figure 11:
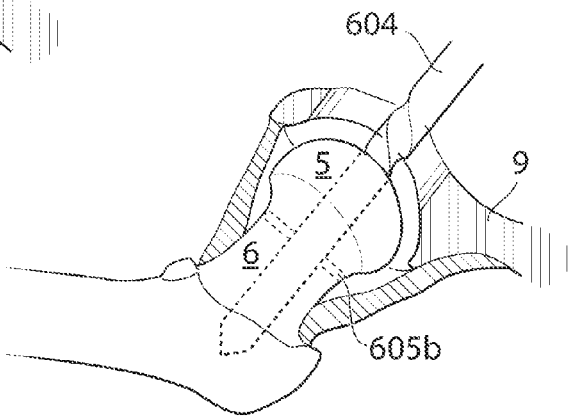
FIG. 11 shows the hip joint in section when a surgical instrument for removing the caput femur is positioned inside of the caput and collum femur.

FIG. 11 shows the hip joint in section when the surgical instrument 604 and the sawing member 605b is positioned inside of the collum femur. After the caput femur 5 has been removed, a stabilizing part of the collum femur 6 is retained. The stabilizing part of collum femur 6 could be defined to be the proximal half of the collum femur 6, the proximal two third of the collum femur, the proximal three quarter of the collum femur, the proximal 90% of the collum femur or the whole collum femur. The proximal part of collum femur being the part of collum femur closest to the torso of the human body.

FIG. 12a-12e shows the medical device and the method of placing said medical device according to a first embodiment.

Figure 12A:
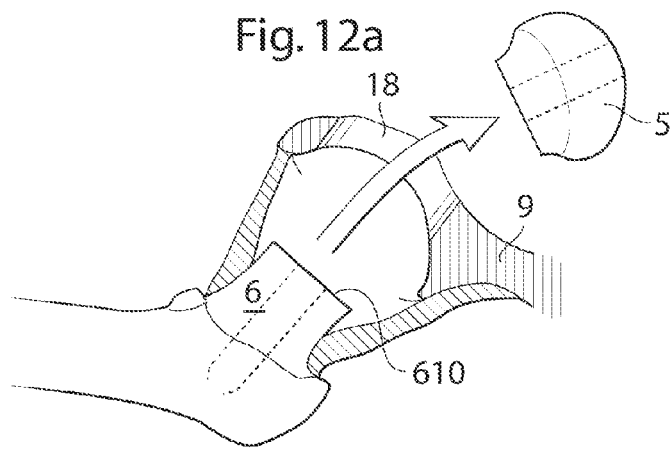
FIGS. 12a and 12b shows the removing of the caput femur through a hole in the femoral bone.

FIG. 12a shows the removal of the caput femur after the surgical instrument 604 has created a surface of a section 610 substantially perpendicularly to the longitudinal extension of the collum femur 6. The separated caput femur 5 is then removed through the hole 18 in the pelvic bone 9.

Figure 12B:
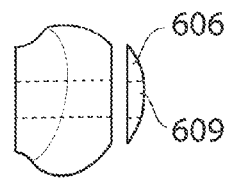

FIG. 12b shows the removal of a piece of bone 606 from the caput femur 5. The removal of the piece of bone 606 is preferably performed outside of the human body. FIG. 12b shows the removal of the top part of caput femur 5; however it is equally conceivable that the piece of bone is removed from any other side of the caput femur 5.

Figure 12C:
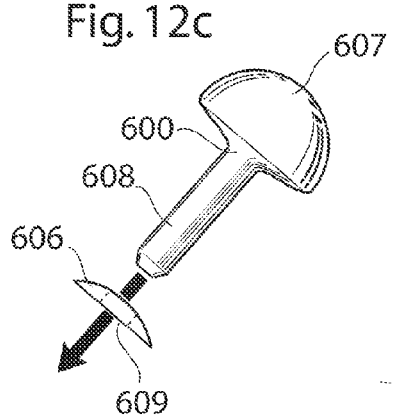
FIG. 12c-12e shows the fixation of a medical device using a piece of bone.

FIG. 12c shows the medical device 600 according to a first embodiment. The medical device comprises a fixating member 608 and an artificial caput femur surface 607. The artificial caput femur surface 607 is adapted to be in contact with the acetabulum surface 11 or an artificial replacement therefor. The fixating member 608 is adapted to at least partly be stabilized by the cortical bone 601 of a stabilizing part of the collum femur 6. The stabilizing could be performed from the inside, substantially perpendicular to the longitudinal extension of the collum femur 6, and from the acetabulum side, substantially in line with the longitudinal extension. The stabilizing could further be performed from the acetabulum side, substantially in line with the longitudinal extension of the collum femur 6, and from the outside, substantially perpendicular to the longitudinal extension of the collum femur, from the inside, substantially perpendicular to the longitudinal extension of the collum femur, and from the outside, substantially perpendicular to the longitudinal extension of the collum femur, or from the acetabulum side, substantially in line with the longitudinal extension of the collum femur, and from the outside, substantially perpendicular to the longitudinal extension of the collum femur. The medical device 600 could be adapted to at least partly be directly stabilized by the cortical bone 601 of said stabilizing part of the collum femur 6, or to be indirectly stabilized by the cortical bone 601 of said stabilizing part of the collum femur 6. In the embodiments (not shown) when the medical device 600 is indirectly stabilized by the cortical bone 601 of the collum femur 6 it is conceivable that a material is placed between said cortical bone 601 and the fixating member 608 of the medical device 600. The material could be: bone cement, an at least partly elastic material, glue, adhesive, antibiotic, biocompatible plastic material, biocompatible ceramics and/or a biocompatible metal such as titanium or tantalum.

The hole 609 in the piece of bone 606 from the caput femur 5 is preferably the hole created by the surgical instrument 604 in the process of removing the caput femur, however it is conceivable that the hole 609 needs to be altered or adapted for fitting the fixating member 608 which is adapted to be placed inside of the hole 609 in the piece of bone 606 removed from the caput femur 5 (also shown in FIG. 12c).

Figure 12D:
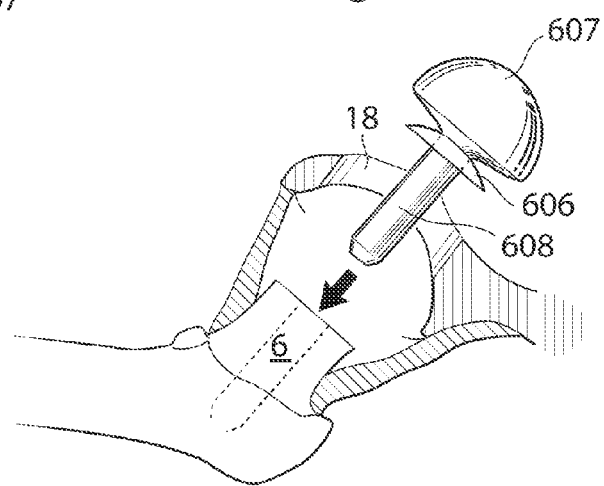

FIG. 12d shows a hip joint in section when the medical device 600, comprises an artificial caput femur surface 607, a fixating member 608 and a stabilizing member 606, being inserted through a hole 18 in the pelvic bone 9. According to this embodiment the stabilizing member is a piece of bone 606 placed on the outside of the fixating member 608. The stabilizing member 606 could be fixated to the fixating member 608 using adhesive or any mechanical connection, such as screws, cord, band or pop-rivets. According to this embodiment the medical device is stabilized by the cortical bone 601 of the collum femur 6 on the inside thereof substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The stabilizing member and the fixating member could be fixated to the collum femur 6 by means of an adhesive or bone cement.

Figure 12E:
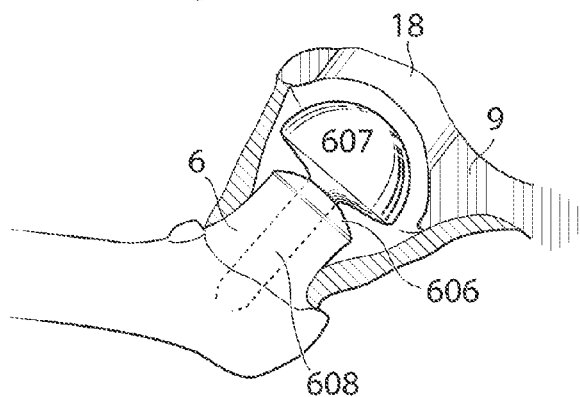

FIG. 12e shows the hip joint in section when the medical device 600, according to the first embodiment, has been placed on the collum femur 6 and is stabilized from the inside thereof by the direct or indirect connection with the cortical bone 601 of the collum femur 6.

FIG. 13a-13e shows the medical device and the method of placing said medical device according to a second embodiment which is not dependant on a particular surgical method, i.e. the surgical method could be a traditional open surgical approach, an arthroscopic approach, or an abdominal approach.

Figure 13A:
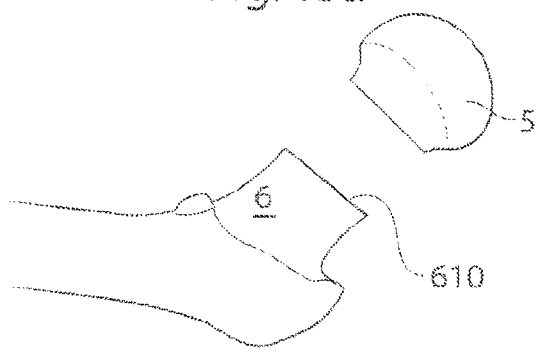
FIGS. 13a and 13b shows the removing of a part of a piece of bone from the caput femur.

FIG. 13a shows the removal of the caput femur after the surgical instrument 604 has created a surface of a section 610 substantially perpendicularly to the longitudinal extension of the collum femur 6. The separated caput femur 5 is then removed through the hole 18 in the pelvic bone 9.

Figure 13B:
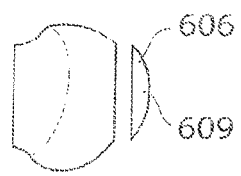

FIG. 13b shows the removal of a piece of bone 609 from the caput femur 5. The removal of the piece of bone 609 is preferably performed outside of the human body. FIG. 13b shows the removal of the top part of caput femur 5; however it is equally conceivable that the piece of bone is removed from any other side of the caput femur 5.

Figure 13C:
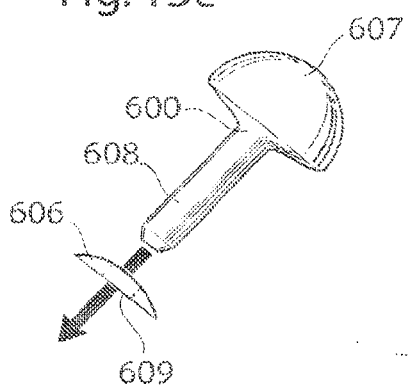
FIG. 13c-13e shows the fixation of a medical device using a piece of bone.

FIG. 13c shows the medical device 600 according to one embodiment. The medical device comprises a fixating member 608 and an artificial caput femur surface 607. The artificial caput femur surface 607 is adapted to be in contact with the acetabulum surface 11 or an artificial replacement therefor. The fixating member 608 is adapted to at least partly be stabilized by the cortical bone 601 of a stabilizing part of the collum femur 6. The stabilizing could be performed from the inside, substantially perpendicular to the longitudinal extension of the collum femur 6, and from the acetabulum side, substantially in line with the longitudinal extension. The stabilizing could further be performed from the acetabulum side, substantially in line with the longitudinal extension of the collum femur 6, and from the outside, substantially perpendicular to the longitudinal extension of the collum femur, from the inside, substantially perpendicular to the longitudinal extension of the collum femur, and from the outside, substantially perpendicular to the longitudinal extension of the collum femur, or from the acetabulum side, substantially in line with the longitudinal extension of the collum femur, and from the outside, substantially perpendicular to the longitudinal extension of the collum femur. The medical device 600 could be adapted to at least partly be directly stabilized by the cortical bone 601 of said stabilizing part of the collum femur 6, or to be indirectly stabilized by the cortical bone 601 of said stabilizing part of the collum femur 6. In the embodiments (not shown) when the medical device 600 is indirectly stabilized by the cortical bone 601 of the collum femur 6 it is conceivable that a material is placed between said cortical bone 601 and the fixating member 608 of the medical device 600. The material could be: bone cement, an at least partly elastic material, glue, adhesive, antibiotic, biocompatible plastic material, biocompatible ceramics and/or a biocompatible metal such as titanium or tantalum.

The hole 609 in the piece of bone 606 from the caput femur 5 could be created before the removal of the caput femur, or after the removal of the caput femur. The hole is adapted for fitting the fixating member 608, which is adapted to be placed inside of the hole 609 in the piece of bone 606 removed from the caput femur 5.

Figure 13D:
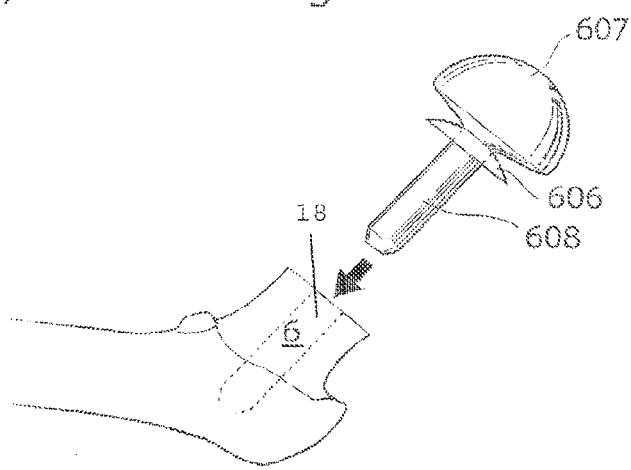

FIG. 13d shows a hip joint in section when the medical device 600, comprises an artificial caput femur surface 607, a fixating member 608 and a stabilizing member 606, being inserted through a hole 18 in the pelvic bone 9. According to this embodiment the stabilizing member is a piece of bone 606 placed on the outside of the fixating member 608. The stabilizing member 606 could be fixated to the fixating member 608 using adhesive or any mechanical connection, such as screws, cord, band or pop-rivets. According to this embodiment the medical device is stabilized by the cortical bone 601 of the collum femur 6 on the inside thereof substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The stabilizing member and the fixating member could be fixated to the collum femur 6 by means of an adhesive or bone cement.

Figure 13E:
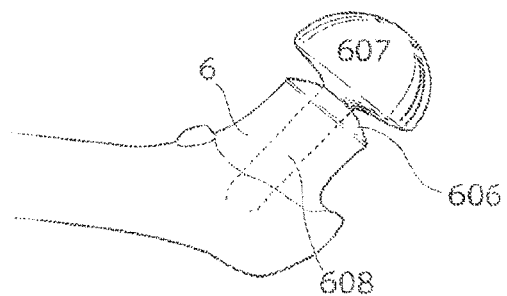
Figure 14A:
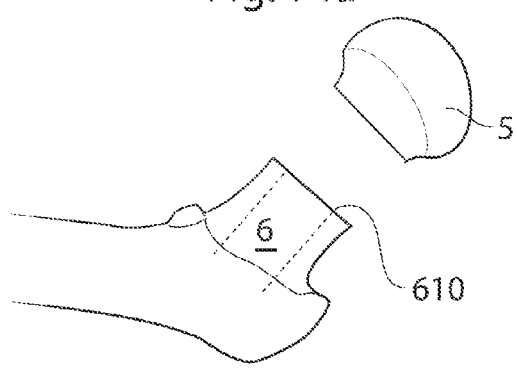
FIGS. 14a and 14b shows the removing of a part of a piece of bone from the caput femur.
Figure 14B:
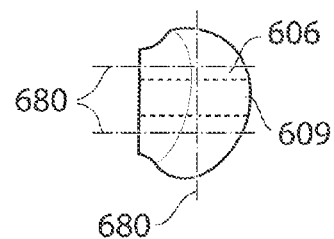
Figure 14C:
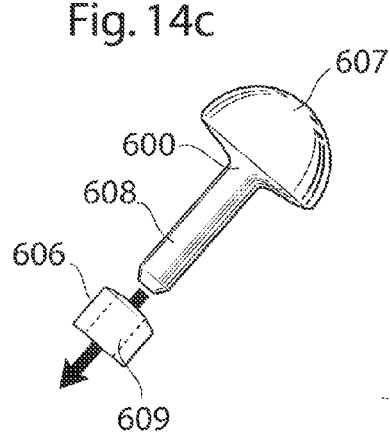
FIG. 14c-14e shows the fixation of a medical device using a piece of bone.
Figure 14D:
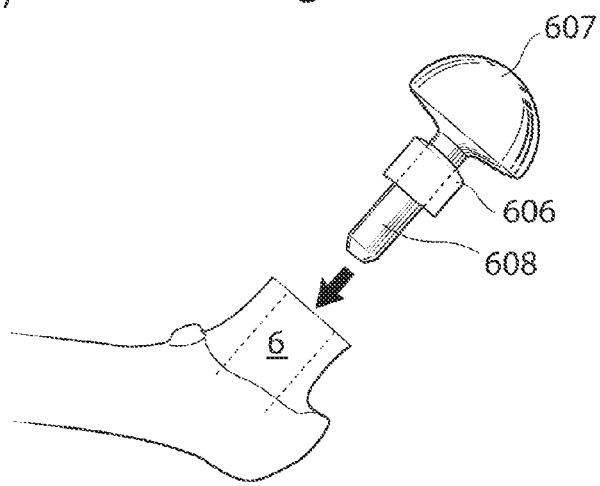
Figure 14E:
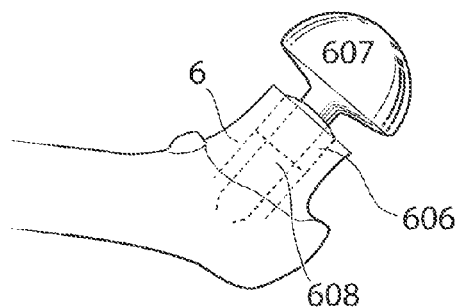
Figure 16A:
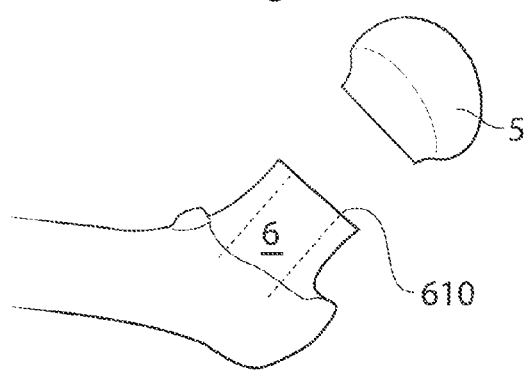
FIGS. 16a and 16b shows the removing of a part of a piece of bone from the caput femur.
Figure 16B:
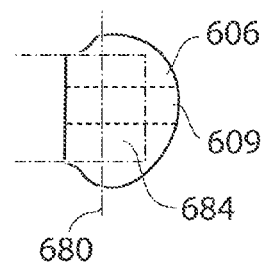
Figure 16C:
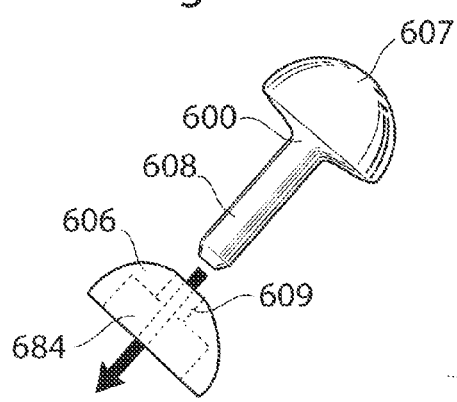
FIG. 16c-16e shows the fixation of a medical device using a piece of bone.
Figure 16D:
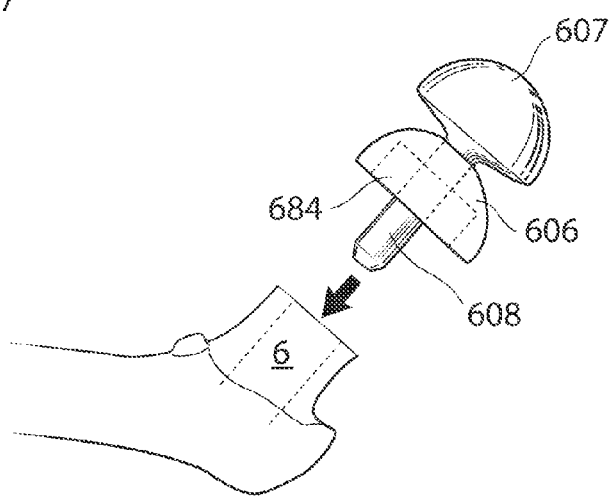
Figure 16E:
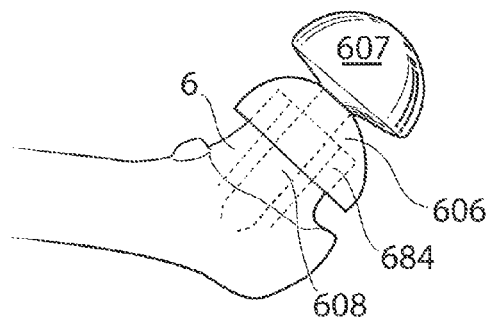
Figure 19A:
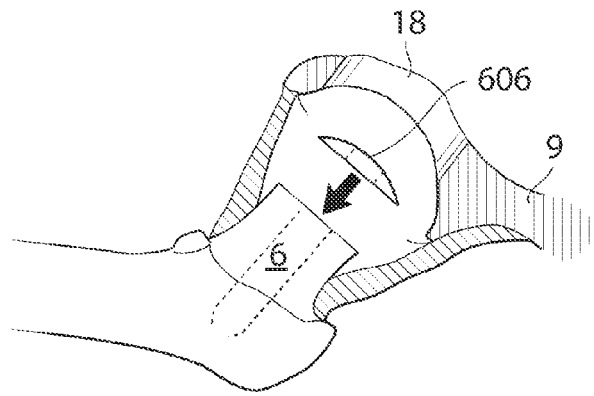
FIG. 19a shows the medical device with the piece of bone being inserted through a hole in the pelvic bone.
Figure 19B:
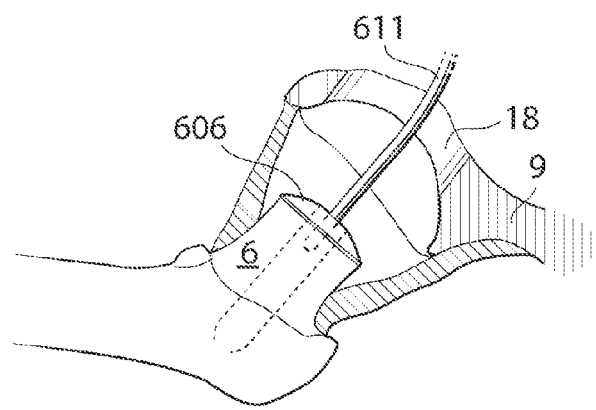
FIG. 19b shows a surgical instrument adapted to fixate the piece of bone to the collum femur.
Figure 20A:
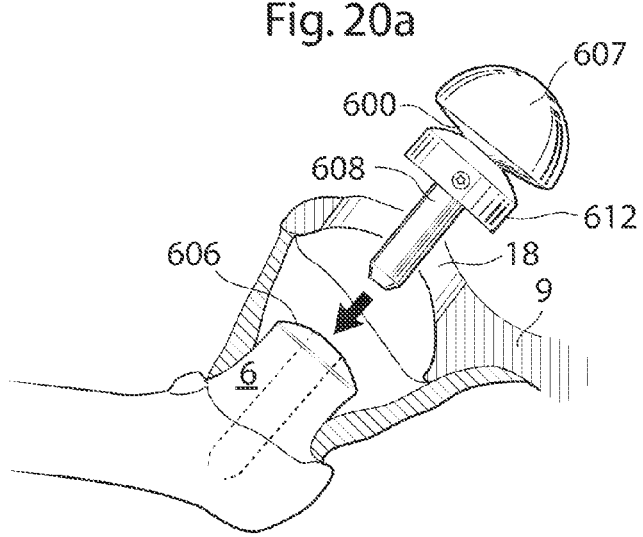
FIG. 20a shows the medical device according to one embodiment, when it is being inserted through a hole in the pelvic bone.
Figure 20B:
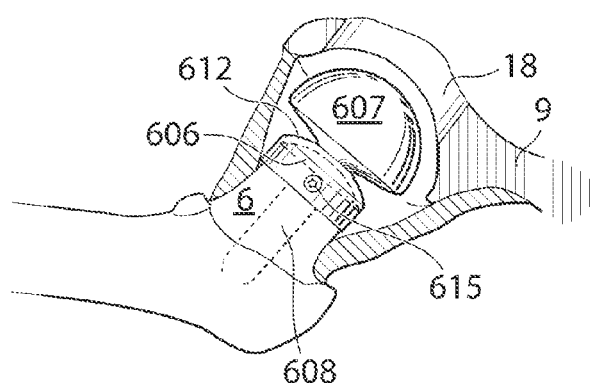
FIG. 20b shows the hip joint in section when the medical device has been provided.

FIG. 13e shows the hip joint in section when the medical device 600, according to the first embodiment, has been placed on the collum femur 6 and is stabilized from the inside thereof by the direct or indirect connection with the cortical bone 601 of the collum femur 6.

FIG. 14a-14e shows the medical device and the method of placing said medical device according to an embodiment similar to the embodiment described with reference to FIGS. 13a-13e. The difference in the embodiment shown in FIGS. 14a-14e is that the piece of bone 606 placed on the fixating member 608 is cut along the cutting lines 680 such that the piece of bone 606 is adapted to be at last partially placed inside of the collum femur 6 for stabilizing the medical device from the inside, substantially perpendicular to the longitudinal extension of the collum femur 6. The piece of bone 606 is according to this embodiment adapted to substantially fill the central parts of the collum femur 6 normally occupied with cancellous bone, such that the cortical bone of the piece of bone 606 comes into contact with the cortical bone of the inside of the collum femur 6 for promoting the growing together of the cortical bone of the collum femur 6 and the cortical bone of the piece of bone 606.

FIG. 15a-15e shows the medical device and the method of placing said medical device according to an embodiment similar to the embodiment described with reference to FIGS. 13a-13e. The difference in the embodiment shown in FIGS. 15a-15e is that the piece of bone 606 placed on the fixating member 608 is cut along the cutting lines 680 such that the piece of bone 606 is adapted to be partially placed inside of the collum femur 6 for stabilizing the medical device from the inside, substantially perpendicular to the longitudinal extension of the collum femur 6 and on the cut surface of the collum femur 6 from the acetabulum side, substantially in line with the longitudinal extension of the collum femur stabilizing the medical device from the acetabulum side of the collum femur 6. The portion of the piece of bone 606 adapted to be placed on the inside of the collum femur 6 is according to this embodiment adapted to substantially fill the central parts of the collum femur 6 normally occupied with cancellous bone, such that the cortical bone of the piece of bone 606 comes into contact with the cortical bone of the inside of the collum femur 6 for promoting the growing together of the cortical bone of the collum femur 6 and the cortical bone of the piece of bone 606.

FIG. 16a-16e shows the medical device and the method of placing said medical device according to an embodiment similar to the embodiment described with reference to FIGS. 13a-13e. The difference in the embodiment shown in FIGS. 16a-16e is that the piece of bone 606 placed on the fixating member 608 is cut along the cutting lines 680 such that the piece of bone 606 is adapted to be partially placed outside of the collum femur 6 for stabilizing the medical device from the outside, substantially perpendicular to the longitudinal extension of the collum femur 6 and on the cut surface of the collum femur 6 from the acetabulum side, substantially in line with the longitudinal extension of the collum femur stabilizing the medical device from the acetabulum side of the collum femur 6. The portion of the piece of bone 606 adapted to be placed on the outside of the collum femur 6 has a cavity adapted to receive a portion of the collum femur 6 or a surgically modified portion of the collum femur 6, such that the cortical bone of the piece of bone 606 comes into contact with the cortical bone of the outside of the collum femur 6 or surgically modified caput femur for promoting the growing together of the cortical bone of the collum femur 6 and the cortical bone of the piece of bone 606. The piece of bone 606 will substantially strengthen the collum femur 6 against axial forces from the fixating member 608 placed inside of the collum femur 6 and create a very stabile position of the artificial caput femur surface 607. The cavity in the piece of bone 606 could for example be created in conjunction with the cutting of the caput femur 5 for creating the piece of bone 606, for example by means of drilling and/or milling.

FIG. 17-20 shows the medical device according to a second embodiment in which a piece of bone 606 from the caput femur 5, or another part comprising cortical bone 601, is positioned on the collum femur 6 before the medical device 600 is introduced in the hip joint. FIGS. 17-20 shows the medical device when used in an abdominal method, in which the medical device is inserted through a hole in the pelvic bone, however, it is equally conceivable that the medical device is stabilized by the collum femur in a conventional open surgical or arthroscopic procedure using an incision placed in the thigh.

FIG. 17a shows the hip joint in section when a piece of bone 606 is being inserted in through the hole 18 in the pelvic bone 9 and being placed on the collum femur 6. The section surface 610 of the collum femur 6 could be supplied with an adhesive or bone cement adapted to fixate the piece of bone 606 to the collum femur 6.

FIG. 17b shows the stabilizing member, here being the piece of bone 606 when fixated to the collum femur 6 using a surgical instrument 611 adapted therefor. The stabilizing member 606 could be fixated to the collum femur 6 using adhesive or any mechanical connection, such as screws, cord, band, pop-rivets and/or form fitting, i.e. the form or shape of the stabilizing member connects it to the collum femur. If the top part of the caput femur 5 is used as piece of bone 606, the piece already comprises a hole 609, which was created by the surgical instrument 604 adapted to remove the caput femur 5, if however the piece of bone 606 is taken from a different part of the caput femur, or a different bone, the hole 609 needs to be created.

FIG. 18a shows the hip joint in section when the medical device 600 is being inserted through a hole 18 in the pelvic bone 9. The medical device comprises a fixating member 608 and an artificial caput femur surface 607. According to this embodiment the medical device is stabilized by the cortical bone 601 of the collum femur 6 on the inside thereof substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6.

FIG. 18b shows the hip joint in section when the medical device 600 is positioned on and inside of the collum femur. The fixating member 608 could be placed in direct or indirect connection with the collum femur. When the medical device 600 is indirectly stabilized by the cortical bone 601 of the collum femur 6 it is conceivable that a material is placed between said cortical bone 601 and the fixating member 608 of the medical device 600. The material could be: bone cement, an at least partly elastic material, glue, adhesive, antibiotic, biocompatible plastic material, biocompatible ceramics and/or a biocompatible metal such as titanium or tantalum.

FIGS. 19a-20b shows an embodiment of the medical device including the elements described with reference to FIGS. 17a-18b. In FIGS. 19a-20b the medical device further comprises a stabilizing member 612 adapted to stabilize the medical device on the outside of the collum femur 6 substantially perpendicular to the longitudinal extension of the collum femur 6. The stabilizing member 612 has an upper portion contacting the collum femur 6 on the acetabulum side of the collum femur 6 and stabilizing the medical device from the acetabulum side thereof and thus covering the piece of bone 606. The embodiment of the stabilizing member is similar to the embodiment shown with reference to FIG. 21a. The stabilizing member could optionally be further fixated by a mechanical fixating element 615, such as a screw.

Figure 21A:
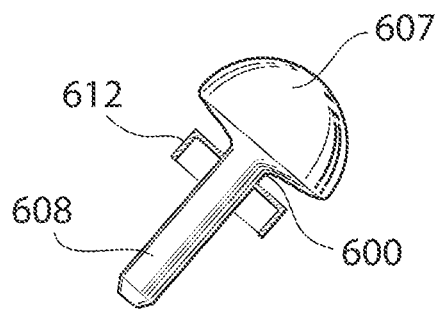
FIG. 21a shows the medical device according to one embodiment, FIG. 21 b shows the medical device according to another embodiment, FIG. 21 c shows the medical device according to yet another embodiment.

FIG. 21a shows the medical device 600 according to an embodiment where the medical device 600 comprises a fixating member 608, an artificial caput femur surface 607 and a stabilizing member 612 adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The stabilizing member 612 and the fixating member 608 could be fixated to the collum femur 6 by means of an adhesive 614 or bone cement. The stabilizing member 612 is made from an artificial material such as a biocompatible metal, (e.g. titanium or tantalum), or a biocompatible polymer or ceramic material. In other embodiments, the stabilizing members 612 could be operable or adjustable for further fixating the medical device to the cortical bone. The stabilizing members 612 could be operable for example by means of a screw for tightening the stabilizing member 612 to the cortical bone, which could squeeze the cortical bone between the stabilizing member 612 and the part of the medical device placed inside of the femoral bone.

Figure 21B:
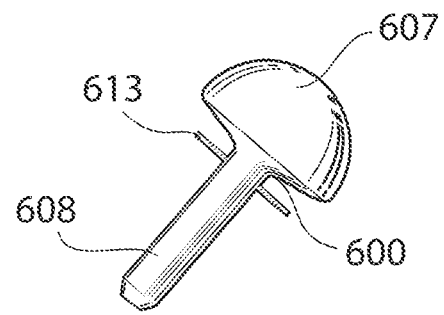

FIG. 21*b* shows the medical device 600 according to an embodiment where the medical device 600 comprises a fixating member 608, an artificial caput femur surface 607 and a stabilizing member 613 adapted to stabilize the medical device 600 from the acetabulum side, substantially in line with the longitudinal extension of the collum femur 6 through the stabilizing member being placed in contact with the surface of a section 610 on the collum femur 6. The stabilizing member 613 and the fixating member 608 could be fixated to the collum femur 6 by means of an adhesive 614 or bone cement. The stabilizing member 613 could be made of an artificial material such as a biocompatible metal, (e.g. titanium or tantalum), or a biocompatible polymer or ceramic material.

Figure 21C:
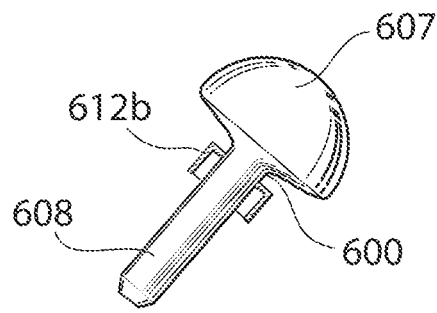

FIG. 21*c* shows the medical device 600 according to an embodiment where the medical device 600 comprises a fixating member 608, an artificial caput femur surface 607 and a stabilizing member 612*b* adapted to stabilize the medical device 600 from the inside of the collum femur 6 substantially perpendicular to the longitudinal extension of the collum femur 6 through the stabilizing member being placed in contact with cortical bone of the collum femur, on the inside thereof. The stabilizing member 612*b* and the fixating member 608 could be fixated to the collum femur 6 by means of an adhesive 614 or bone cement. The stabilizing member 612*b* could be made of an artificial material such as a biocompatible metal, (e.g. titanium or tantalum), or a biocompatible polymer or ceramic material.

Figure 22:
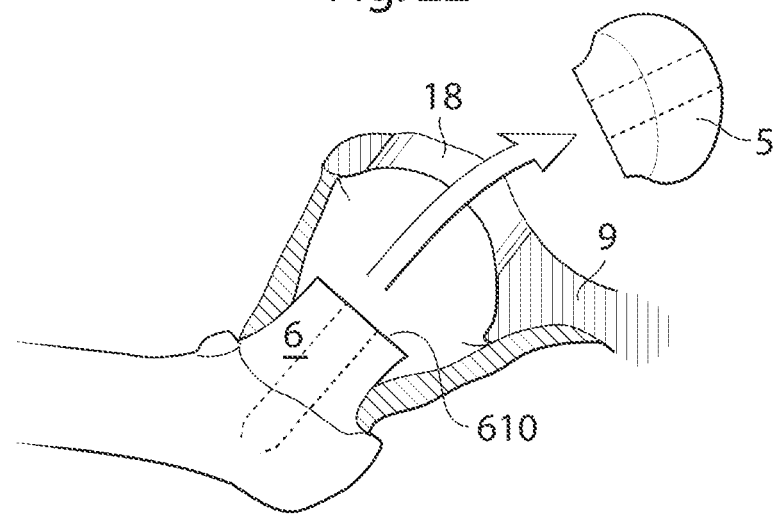
FIG. 22 shows the hip joint in section when the caput femur is being removed through a hole in the femoral bone.

FIG. 22 shows the hip joint in section when the caput femur 5 is being removed through a hole 18 in the pelvic bone 9. The step of removing the caput femur 5 needs to be performed before the medical device 600 according to the embodiments shown in FIGS. 21*a* and 21*b* can be positioned in the hip joint.

FIG. 23*a* shows the hip joint in section in the step in which the surface of the section 610 in the collum femur 6 is prepared. An injecting member 613 applies and adhesive 614 to the surface of the section 610 of the collum femur 6. The injecting member 613 is adapted to be introduced through a hole 18 in the pelvic bone 9 and to apply the adhesive 614 which was contained within the injecting member 613.

FIG. 23*b* shows the step of introducing and fixating the medical device according to FIG. 21*a* to the collum femur 6, through a hole 18 in the pelvic bone 9. The stabilizing member 612*a* is adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member being placed in contact with the outside of the collum femur 6 and the surface of the section 610 in the collum femur 6. The stabilizing member 612 is fixated to the outside of the collum femur 6 and/or to the surface of the section 610 in the collum femur 6 by means of the adhesive 614. However the adhesive 614 could be replaced or assisted by bone cement or a mechanical fixation element 615.

FIG. 24*a* shows the hip joint in section when the medical device 600 is positioned on the collum femur 6. The stabilizing member 612*a* is here fixated to the collum femur by means of adhesive 614 and a mechanical fixation element 615.

FIG. 24*b* shows the hip joint in section when the medical device 600 is positioned on the collum femur 6. The stabilizing member 613 is here fixated to the collum femur by means of adhesive 614.

Figure 25A:
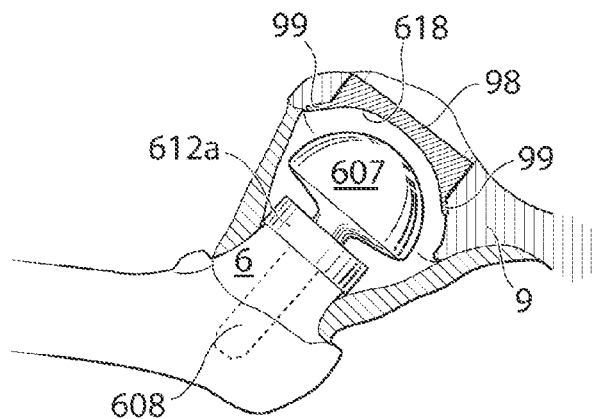
FIG. 25a shows the step of placing a prosthetic part in the hole in the pelvic bone.

FIG. 25*a* shows the hip joint in section when the medical device 600 is positioned on the collum femur 6. The stabilizing member 612*a* is here fixated to the collum femur by means of adhesive 614. A prosthetic part 98 comprising an artificial acetabulum surface 618 has been positioned in the hole 18 in the pelvic bone 9. The artificial acetabulum surface 618 is adapted to be in direct of indirect connection with the artificial caput femur surface 607. In embodiments where the artificial acetabulum surface 618 is adapted to be in indirect connection with the artificial caput femur surface 607 a lubricating fluid or a lubricating material (not shown) can be placed between said artificial acetabulum surface 618 and said artificial caput femur surface 607. The prosthetic part is adapted to carry the load placed on the artificial acetabulum surface 618 from weight of the human patient through the contact with the artificial caput femur surface 607 by means of the supporting members 99. The prosthetic part 98 can further be fixated to the pelvic bone 9 by means of bone cement, adhesive, screws, form fitting, welding, sprints, band or some other mechanical connecting member. According to this embodiment the supporting members 99 are positioned on the acetabulum side of the pelvic bone 9, however it is also conceivable that the supporting members 99 are positioned on the abdominal side of the pelvic bone 9.

Figure 25B:
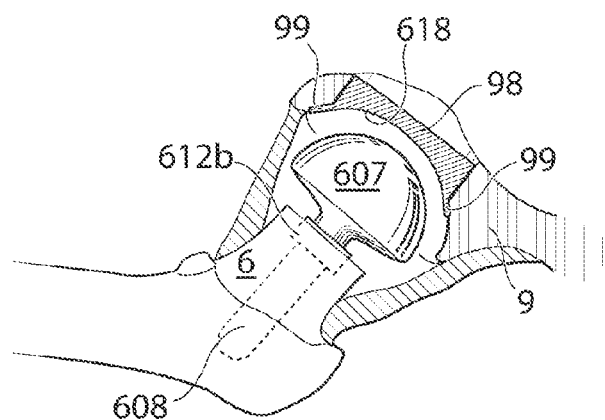
FIG. 25b shows the step of placing a prosthetic part in the hole in the pelvic bone.

FIG. 25*b* shows the hip joint in section when the medical device 600 is positioned on the collum femur 6. The stabilizing member 612*b* is here fixated to the collum femur by means of adhesive 614 on the inside thereof. The stabilizing member is placed in contact with the cortical bone of the 601 of the collum femur 6 and the medical device 600 is thereby stabilized by the collum femur. A prosthetic part 98 comprising an artificial acetabulum surface 618 has been positioned in the hole 18 in the pelvic bone 9. The artificial acetabulum surface 618 is adapted to be in direct of indirect connection with the artificial caput femur surface 607. In embodiments where the artificial acetabulum surface 618 is adapted to be in indirect connection with the artificial caput femur surface 607 a lubricating fluid or a lubricating material (not shown) can be placed between said artificial acetabulum surface 618 and said artificial caput femur surface 607. The prosthetic part is adapted to carry the load placed on the artificial acetabulum surface 618 from weight of the human patient through the contact with the artificial caput femur surface 607 by means of the supporting members 99. The prosthetic part 98 can further be fixated to the pelvic bone 9 by means of bone cement, adhesive, screws, form fitting, welding, sprints, band or some other mechanical connecting member. According to this embodiment the supporting members 99 are positioned on the acetabulum side of the pelvic bone 9, however it is also conceivable that the supporting members 99 are positioned on the abdominal side of the pelvic bone 9.

Figure 26:
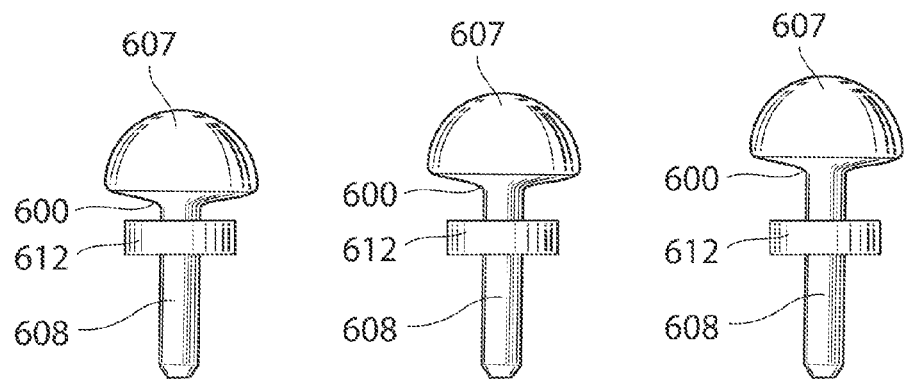
FIG. 26 shows three embodiments of the medical device.

FIG. 26 shows that the medical device 600 needs to be adapted to the collum femur 6. Both the distance between the stabilizing member 612 and the artificial caput femur surface 607 and the length of the fixating member could need adjustment to the stabilizing pert of the collum femur. The stabilizing part of collum femur 6 could be defined to be the proximal half of the collum femur 6, the proximal two third of the collum femur, the proximal three quarter of the collum femur, the proximal 90% of the collum femur or the whole collum femur, and the medical device needs to be adapted accordingly.

Figure 27:
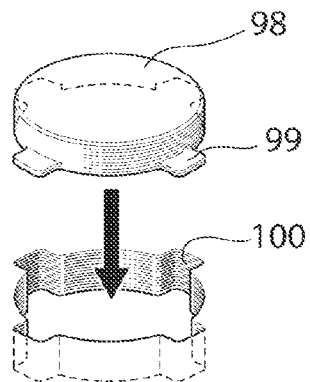
FIG. 27 shows a conceptual view of the prosthetic part adapted to be placed in the hole in the pelvic bone.

FIG. 27 shows a prosthetic part 98 being inserted into a hole 18 in the pelvic bone 9 from the opposite side from acetabulum. According to one embodiment the prosthetic part 98 comprises supporting members 99 adapted to correspond with sections 100 of the hole 18 in the pelvic bone 9. After the prosthetic part 98 has been inserted using a surgical instrument it is rotated so that the supporting members 99 comes in contact with the pelvic bone 9 and can carry the load placed on the artificial acetabulum surface. Said prosthetic part 98 could also be adapted to serve as artificial acetabulum surface 618 according to any of the above mentioned embodiments.

Figure 28:
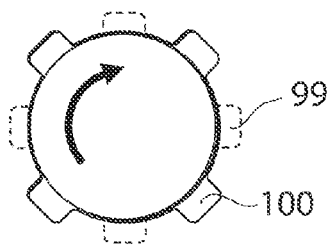
FIG. 28 shows a conceptual view of the function of the prosthetic part adapted to be placed in the hole in the pelvic bone.

FIG. 28 shows the prosthetic part 98 when rotated to carry the load placed on the artificial acetabulum surface from weight of the human patient.

Figure 29:
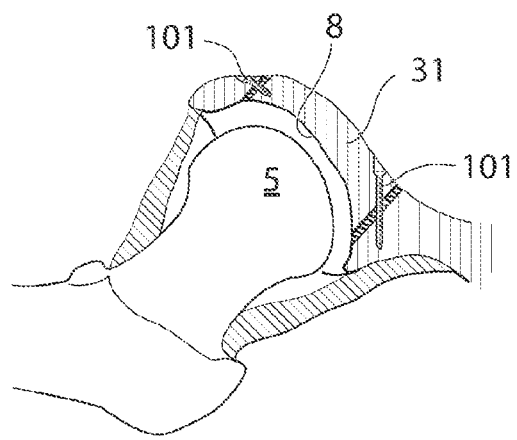
FIG. 29 shows the step of fixating a piece of bone in a hole in the pelvic bone.

FIG. 29 shows the hip joint of a human patient in section wherein bone plug 31 is attached to the pelvic bone 9 by means of screws 101 placed from the opposite side from acetabulum 8. The screws 101 are possible to place in different angles depending on reach or need for support. The bone plug could be adapted to comprise the artificial acetabulum surface 618, or it can be placed on top of said artificial acetabulum surface 618 to support and covert the hole 18 made in the pelvic bone 9.

Another approach to replacing the caput femur and acetabulum surfaces will now be described, wherein a concave hip joint surface is placed in connection with the collum femur and a convex hip joint surface is placed in connection with the pelvic bone.

FIG. 30 shows the caput femur 5 after the proximal part has been removed along the section created by the medical device for creating a hole. The removing of the proximal part of the caput femur 5 creates a surface of a section 102 in the cortical bone of the caput femur 5. A reamer 40 adapted to create a concave surface 103 in the caput femur 5 is applied to the force transferring member 21 through a connecting section 101. According to this embodiment the force transferring member 21 is the same as the force transferring member used for the medical device adapted to create a hole in the pelvic bone 9, however it is equally conceivable that the force transferring member 21 is specifically designed to enable the reaming of the caput femur 5. The reaming in the caput femur and part of the collum femur 6 is mainly performed in the cancellous bone, however that does not exclude the possibility the some of the reaming needs to be performed in the cortical bone of the caput femur 5 and/or the collum femur 6.

FIG. 31 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

FIG. 32 shows the step of providing a medical device 109 comprising an artificial concave hip joint surface 110. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a inserting member 107. According to this embodiment the inserting member is bent and thereby adapted to operate through a hole 18 in the pelvic bone 9. The inserting member 107 comprises a connecting member 108 which is adapted to connect to the medical device 109. According to one embodiment the medical device 109 comprises a self lubricating material such as PTFE, however it is also conceivable that said medical device comprises: titanium, stainless steel, corian, PE, or other acrylic polymers, in which case the medical device could be adapted to be lubricated after insertion in the hip joint.

Figure 33:
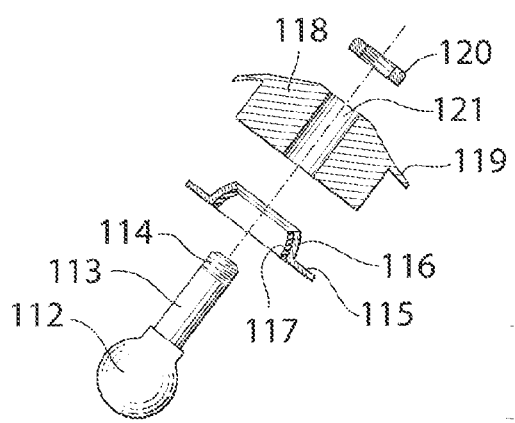
FIG. 33 shows the parts of a medical device according to another embodiment.

FIG. 33 shows a medical device comprising an artificial convex hip joint surface 112. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking element 116 comprising a surface 117 adapted to be in contact with the artificial convex hip joint surface 112. The locking element 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to a attachment rod 113 comprising a thread 114 that corresponds to the thread of the nut 120 in connection with the prosthetic part 118.

Figure 34:
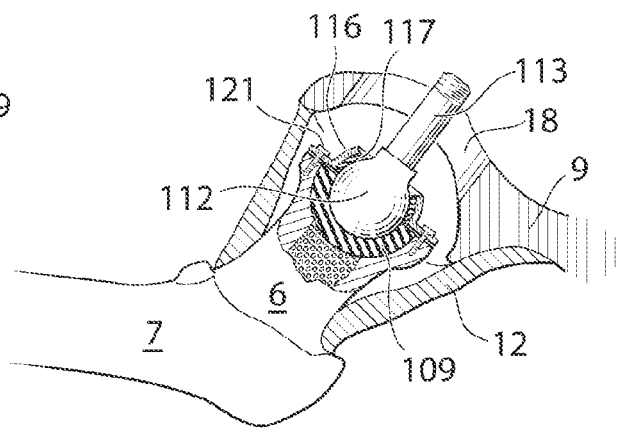
FIG. 34 shows the hip joint in section when a medical device has been provided.

FIG. 34 shows the hip joint in section when the artificial convex hip joint surface is fixated in the medical device 109 comprising a concave hip joint surface 110. The convex hip joint surface 112 is secured in place by the locking element 116 which is fixated to the caput femur using screws 121. The surface of the locking element 117 and the concave hip joint surface 117 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient.

Figure 35:
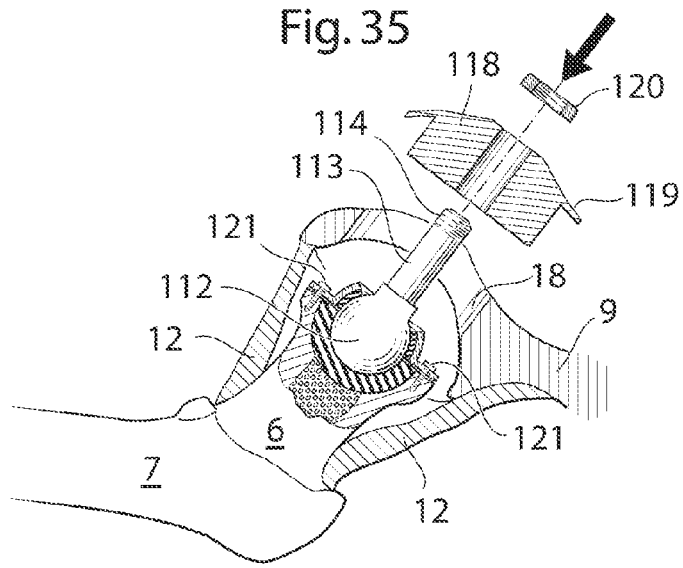
FIG. 35 shows the placing of a prosthetic part in the hole in the pelvic bone.

FIG. 35 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. According to the embodiment shown in FIG. 35 the supporting members 119 are located on the abdominal side of the pelvic bone 9, however it is equally conceivable the supporting members 119 are located on the acetabulum side of the pelvic bone 9, in which case they are preferably displaceable for allowing insertion of the prosthetic part 118 through the hole 18 in the pelvic bone 9. Furthermore the fixation of a nut 120 to the attachment rod 113 is shown. According to one embodiment the hole 18 in the pelvic bone 9 is adapted to be larger than the medical device allowing the medical device to be inserted in its full functional size. According to other embodiments the hole 18 is smaller in which case the medical device could comprise of several parts adapted to be connected after insertion in the hip joint, or the medical device could be expandable for insertion through a hole smaller than the full functional size of the medical device. The expandable medical device could be enabled through the elements of the medical device comprising elastic material.

Figure 36:
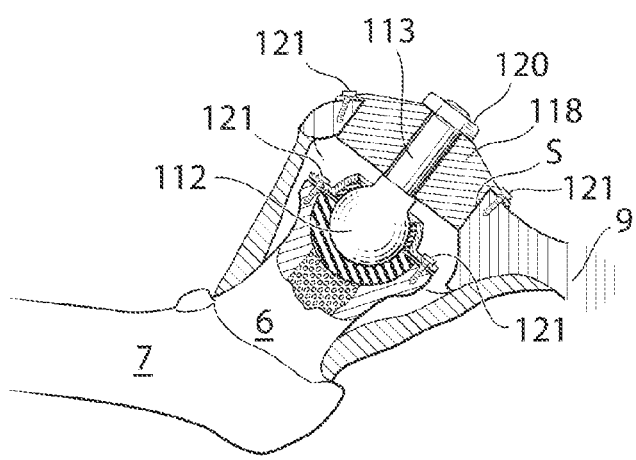
FIG. 36 shows a section of the hip joint when a medical device has been fixated.

FIG. 36 shows the hip joint in section when all the elements of the medical device has been fixated in the area of the hip joint or its surroundings. The prosthetic part 113 adapted to occupy the hole 18 in the pelvic bone 9 is here fixated with screws 121, however these screws 121 could be assisted or replaced by an adhesive which could be applied to the surface S between the prosthetic part and the pelvic bone 9.

In the above embodiments the medical device 600 have been described in the context of a surgical procedure from the abdominal side of the pelvic bone, however it is also conceivable that the medical device is inserted through the a hole in the femoral bone or a hole in the hip joint capsule, and is adapted therefor. A conceptual view of the embodiment where the medical device 600 is inserted through the hip joint capsule is illustrated in FIG. 4, what is commonly described as conventional hip joint surgery.

The fixating member and/or the artificial caput femur and acetabulum could comprise stainless steel, titanium or titanium alloys. The fixating member could be adapted to be porous for improving the growth of bone in connection with the medical device. The surface areas of the artificial acetabulum and/or the caput femur could comprise a fluoropolymer material, however there could also be an intermediary part between said artificial caput femur and said artificial acetabulum surface which could comprise a flourpolymer material.

Please note that any embodiment or part of embodiment as well as any method or part of method could be combined in any way. All examples herein should be seen as part of the general description and therefore possible to combine in any way in general terms.

The invention claimed is:

1. A medical device for treating hip joint osteoarthritis in a human patient, the hip joint comprising an acetabulum being a part of a pelvic bone, and a caput femur being connected to a collum femur and being an upper extremity of a femoral bone, the caput femur and collum femur further comprising cortical bone, an outer more sclerotic bone, and cancellous bone, placed in a bone marrow, the medical device comprising:
   an artificial caput femur surface adapted to be in contact with an acetabulum surface or an artificial replacement therefor, and
   a fixating member adapted to at least partly be stabilized by the cortical bone of a stabilizing part of the collum femur, wherein the medical device further comprises a stabilizing member formed by a piece of natural cortical bone from the caput femur, previously removed from the caput femur, said stabilizing member being adapted to be connected to the cortical bone of the collum femur, wherein at least a portion of the stabilizing member is adapted to be placed inside of the collum femur between the cortical bone of the collum femur and the fixating member, for fixating the fixating member to the collum femur.

2. The medical device according to claim 1, wherein at least a portion of the stabilizing member is adapted to be placed on a cut side of the collum femur facing the acetabulum for stabilizing the medical device from the acetabulum side of the collum femur.

3. The medical device according to claim 2, wherein the fixating member is adapted to be at least partly stabilized by the cortical bone of a stabilizing part of the collum femur, from the inside of the collumn femur, substantially perpendicular to a longitudinal extension of the collum femur, and from the acetabulum side of the collum femur, substantially in line with the longitudinal extension.

4. The medical device according to claim 3, wherein the stabilizing part of collum femur is defined to be at least one of:
   a proximal half of the collum femur,
   a proximal two thirds of the collum femur,
   a proximal three quarters of the collum femur,
   a proximal 90% of the collum femur, and
   the whole collum femur.

5. The medical device according to claim 4, wherein the fixating member is adapted to be at least partly directly stabilized by the cortical bone of the stabilizing part of the collum femur.

6. The medical device according to claim 1, wherein the fixating member is an elongated fixating member adapted to be inserted into the collum femur, and wherein the elongated member extends through the stabilizing member.

7. The medical device according to claim 1, wherein the fixating member is adapted to be positioned on the collum femur.

8. The medical device according to claim 1, wherein the medical device further comprises a stabilizing element adapted to stabilize the medical device on the outside of the collum femur, and wherein the stabilizing element is adapted to at least partially cover the stabilizing member on an acetabulum side of the piece of bone.

9. The medical device according to claim 1, wherein the fixating member further comprises a mechanical connection adapted to mechanically connect to the cortical bone of the stabilizing part of the collum femur on at least the outside thereof.

10. The medical device according to claim 1, wherein at least a portion of the stabilizing member is adapted to be placed on at least one of:
   the inside of the collum femur for stabilizing the medical device from the inside of the collum femur, and
   a cut side of the collum femur facing the acetabulum for stabilizing the medical device from the acetabulum side of the collum femur.

11. A medical device for treating hip joint osteoarthritis in a human patient, the hip joint comprising an acetabulum being a part of a pelvic bone, and a caput femur being connected to a collum femur and being an upper extremity of a femoral bone, the caput femur and collum femur further comprising cortical bone, an outer more sclerotic bone, and cancellous bone, placed in a bone marrow, the medical device comprising:
   an artificial caput femur surface adapted to be in contact with an acetabulum surface or an artificial replacement therefor, and
   a fixating member adapted to at least partly be stabilized by the cortical bone of a stabilizing part of the collum femur, wherein the medical device further comprises a stabilizing member formed by a piece of natural cortical bone from the caput femur, previously removed from the caput femur, said stabilizing member being adapted to be connected to the cortical bone of the collum femur, wherein at least a portion of the stabilizing member is adapted to be placed on a cut side of the collum femur facing the acetabulum for stabilizing the medical device from the acetabulum side of the collum femur, for stabilizing the fixating member.

12. The medical device according to claim 11, wherein the fixating member is an elongated fixating member adapted to be inserted into the collum femur, and wherein the elongated member extends through the stabilizing member.

13. The medical device according to claim 11, wherein at least a portion of the stabilizing member is adapted to be placed inside of the collum femur between the cortical bone of the collum femur and the fixating member, for fixating the fixating member to the collum femur.

14. The medical device according to claim 11, further comprising a stabilizing element adapted to stabilize the medical device on the outside of the collum femur, and wherein the stabilizing element is adapted to at least partially cover the stabilizing member on an acetabulum side of the piece of bone.

15. The medical device according to claim 14, further comprising a mechanical fixating element configured to fixate the stabilizing element to the collum femur.

16. A medical device for treating hip joint osteoarthritis in a human patient, the hip joint comprising an acetabulum being a part of a pelvic bone, and a caput femur being connected to a collum femur and being an upper extremity of a femoral bone, the caput femur and collum femur further comprising conical bone, an outer more sclerotic bone, and cancellous bone, placed in a bone marrow, the medical device comprising:
- an artificial caput femur surface adapted to be in contact with an acetabulum surface or an artificial replacement therefor, and
- a fixating member adapted to at least partly be stabilized by the cortical bone of a stabilizing part of the collum femur, wherein the fixating member further comprises a stabilizing element, said stabilizing element being adapted to be connected to the cortical bone of the collum femur, wherein the stabilizing element is adapted to be placed on a cut side of the collum femur facing the acetabulum for stabilizing the medical device from the acetabulum side of the collum femur.

17. The medical device according to claim 16, wherein said stabilizing element is further adapted to also at least partly cover the outside of the collum femur for stabilizing the medical device from the outside of the collum femur.

18. The medical device according to claim 16, further comprising a mechanical fixating element configured to fixate the stabilizing element to the collum femur.

* * * * *